ns Patent [19] [11] 4,073,934
Skuballa et al. [45] Feb. 14, 1978

[54] NOVEL ACETYLENIC PROSTAGLANDIN ANALOGS

[75] Inventors: Werner Skuballa; Bernd Radüechel; Helmut Vorbrueggen; Walter Elger; Olaf Loge; Eckehard Schillinger, all of Berlin, Germany

[73] Assignee: Schering Aktiengesellschaft, Berlin and Bergkamen, Germany

[21] Appl. No.: 677,861

[22] Filed: Apr. 16, 1976

[30] Foreign Application Priority Data

Apr. 18, 1975 Germany .............................. 2517771

[51] Int. Cl.² ................. C07C 177/00; A61K 31/215; A61K 31/19
[52] U.S. Cl. ................................ 424/305; 260/295 R; 260/332.2 A; 260/345.7 P; 260/345.8 P; 260/346.2; 260/347.3; 260/347.4; 260/448.8 R; 260/501.17; 260/514 D; 260/520 B; 260/556 A; 424/275; 424/285; 424/263; 424/308; 424/317; 424/321; 560/53; 560/60; 560/106; 560/121; 560/255; 542/426
[58] Field of Search ...................... 260/468 D, 514 D; 424/305, 317

[56] References Cited
FOREIGN PATENT DOCUMENTS 140,427 11/1975 Japan .................................... 260/468

Primary Examiner—Robert Gerstl
Attorney, Agent, or Firm—Millen & White

[57] ABSTRACT

Optically active and racemic prostaglandin derivatives of the formula wherein $R_1$ is $-OR_5$; $-NHSO_2CH_3$; or $-O-CH_2-U-V$; $R_5$ is hydrogen, alkyl, aryl, or a heterocyclic group; U is a direct bond, carbonyl or carbonyloxy; and V is phenyl substituted by 1-3 phenyl, alkoxy of 1-2 carbon atoms, or halogen, preferably bromine;

$R_2$ is hydrogen or alkyl of 1-5 carbon atoms;

$R_3$ is alkyl, substituted or unsubstituted cycloalkyl, straight-chain or branched alkyl of 1-5 carbon atoms substituted by aryl or substituted aryl, when $R_1$ is as above; or $R_3$ is aryl or substituted aryl group when $R_1$ is $-OR_5'$, $-NHSO_2CH_3$, or $-O-CH_2-U-V$ and $R_5'$ is aryl or a heterocyclic group and U and V are as above;

$R_4$ is hydrogen or an ether or acyl residue;

A is $-CH_2-CH_2-$ or cis$-CH=CH-$;

B is $-CH_2-CH_2-$ or trans$-CH=CH-$;

D is a direct bond, oxygen, or sulfur;

Z is carbonyl or $>CH\sim\sim OR_4$ wherein $OR_4$ is in the $\alpha$- or $\beta$-position; and X $===$ Y is $$-CH_2-\underset{OR_4}{\underset{\equiv}{CH}}-\quad \text{or} \quad -CH_2-\underset{\underset{O}{\parallel}}{C}-$$

when Z is $>CH\sim\sim OR_4-$, or $$-CH_2-\underset{OR_4}{\underset{\equiv}{CH}}-$$

or $-CH=CH-$ when Z is carbonyl;

and, when $R_1$ is hydroxy, the physiologically compatible salts thereof with bases, have more prolonged activity than naturally-occurring prostaglandins.

82 Claims, No Drawings

NOVEL ACETYLENIC PROSTAGLANDIN ANALOGS

BACKGROUND OF THE INVENTION

This invention relates to novel acetylenic prostaglandin compounds and a process for the preparation thereof.

The physiological effects of naturally-occurring prostaglandins in the mammalian organism and in vitro are only of a brief duration, since prostaglandins are rapidly converted to a plurality of pharmacologically inactive metabolic products. Moreover, natural prostaglandins do not possess any biological specificity, which is necessary for a medicinal agent.

Therefore, there is a need for prostaglandin analogs with a spectrum of activity comparable to that of the natural prostaglandins but in which the duration and selectivity of the effectiveness are increased.

It has now been found that prostaglandin derivatives with a triple bond between the C-16 and C-17 carbon atoms possess surprisingly a longer duration of activity, higher selectively, and a higher effectiveness than natural prostaglandins.

SUMMARY OF THE INVENTION

In a compositional aspect, this invention relates to a prostaglandin compound of Formula I

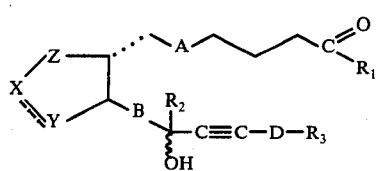

wherein $R_1$ is $-OR_5$, $-NHSO_2CH_3$ or $-O-CH_2-U-V$, $R_5$ being a hydrogen atom, or an alkyl, aryl, or heterocyclic group, U being a direct bond, carbonyl or carbonyloxy, and V being a phenyl ring substituted by one or more of phenyl, alkoxy of 1-2 carbon atoms, and halogen, preferably bromine;

$R_2$ is hydrogen or alkyl of 1-5 carbon atoms;

$R_3$ is alkyl, cycloalkyl or alkylaryl of up to 10 carbon atoms, furyl, thienyl, pyridyl or aryl;

A is $-CH_2-CH_2-$ or cis-$CH=CH-$;

B is $-CH_2-CH_2-$ or trans-$CH=CH-$;

D is a direct bond, oxygen, or sulfur;

Z is carbonyl or $> CH\sim\sim OR_4$—wherein $OR_4$ is a free, esterified or etherified hydroxy group in the α- or β-position; and X≡≡≡Y is

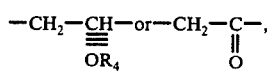

when Z is $> CH\sim\sim OR_4$—, or

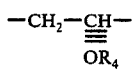

or $-CH=CH-$, when Z is carbonyl;

including both the optically active and racemic forms thereof and, when $R_1$ is hydroxy, physiologically acceptable salts thereof with bases.

In another aspect, this invention relates to a process for the preparation of 16,17-acetylene-prostaglandins of Formula I, wherein, in a conventional manner;

a. a compound of Formula II

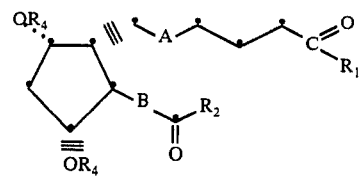

wherein $R_1$, $R_2$, $R_4$ A, and B are as above, is reacted with an organometallic acetylene compound of Formula III

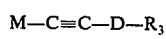

wherein $R_3$ and D are as above and

M is a metal-containing residue; or b. a lactol of Formula IV

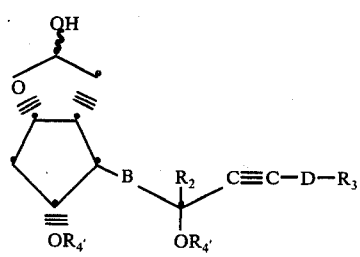

wherein $R_2$, $R_3$ and D are as above and $R_4$ is an ether residue, is reacted with a Wittig reagent of Formula V

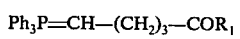

and Ph is phenyl group and $R_1$ is as above; and c. optionally, in any desired succession, thereafter a free carboxy group is esterified or an esterified carboxy group is saponified and/or a 9-keto group is reduced and/or a 9-keto compound is dehydrated while an 11-hydroxy group is eliminated and/or a 9-hydroxy group is oxidized after first blocking 11- and 15-hydroxy groups and/or a 9-hydroxy group or an 11-hydroxy group is oxidized regioselectively, optionally after first blocking the 15-hydroxy group and/or a free OH-group is functionally modified and/or a functionally modified OH-group is liberated, and a 1-carboxy compound is converted with a base into a physiologically compatible salt and, optionally, the racemates are separated.

In another compositional aspect, this invention relates to a luteolytic pharmaceutical composition, comprising a compound of Formula I, in admixture with a pharmaceutically acceptable carrier.

DETAILED DISCUSSION $R_2$ is straight-chain and branched-chain alkyl of 1-5 carbon atoms, for example, methyl, ethyl, propyl, isopropyl, butyl, isobutyl, and pentyl. Methyl and ethyl groups are preferred.

Substituted and/or unsubstituted aryl $R_5$ and $R_3$ are, for example, phenyl, 1-naphthyl, and 2-naphthyl, each of which can be substituted by up to 3 of halogen, phenyl, alkyl of 1-4 carbon atoms, chloromethyl, fluoromethyl, trifluoromethyl, carboxy, alkoxy, or hydroxy.

$R_5$ and $R_3$ alkyl are straight-chain and branched, saturated and unsaturated alkyl, preferably saturated alkyl residues of 1-10, most preferably 1-6, carbon atoms. Examples are methyl, ethyl, propyl, butyl, isobutyl, tert.-butyl, pentyl, hexyl, heptyl, octyl, butenyl, isobutenyl, propenyl, and pentenyl groups.

Heterocyclic groups $R_5$ and 5- and 6-membered heterocycles containing at least one hetero atom, preferably nitrogen, oxygen, or sulfur. Examples include, but are not limited to, 2-furyl, 2-thienyl, 2-pyridyl and 3-pyridyl.

$R_3$ cycloalkyl can contain 4–10 carbon atoms in the ring, which can be substituted by alkyl groups of 1-4 carbon atoms. Examples are cyclopentyl, cyclohexyl, ethylcyclohexyl, and adamantyl.

$R_4$ ether and acyl are those known to a person skilled in the art. Examples of ether residues are tetrahydropyranyl, tetrahydrofuranyl, α-ethoxyethyl, trimethylsilyl, and tri-p-xylysilyl. Acyl include alkanoyl and aroyl of up to 7 carbon atoms, preferably acetyl, propionyl, butyryl, and benzoyl.

Suitable for salt formation are inorganic and organic bases familiar to those skilled in the are of forming physiologically compatible and pharmacologically acceptable salts. Examples are alkali metal hydroxides, such as sodium or potassium hydroxide; alkaline earth hydroxides, such as calcium hydroxide; ammonia; amines, such as ethanolamine, diethanolamine, triethanolamine, N-methylglucamine, morpholine, and tris(hydroxymethyl)methylamine.

Preferred compounds of this invention are compounds of Formula I, wherein:

a. the compound is the free acid;
b. the compound is in the form of a methyl ester;
c. the compound is in the form of a methylsulfonylamide;
d. The compound is in the form of a biphenylyl ester;
e. the compound is in the form of a tris(hydroxymethyl)aminomethane salt;
f. the compound is in the form of a p-phenyl-phenacyl ester;
g. $R_3$ is alkyl of 1-5 carbon atoms, including (a)–(g);
h. D is oxygen, including (a)–(g);
i. D is oxygen and $R_3$ is alkyl or aryl, including (a)–(g);
j. D is a direct bond and $R_3$ is furyl, including (a)–(g);
k. D is a direct bond and $R_3$ is thienyl, including (a)–(g);
l. D is a direct bond and $R_3$ is pyridyl, including (a)–(g);
m. D is a direct bond and $R_3$ is cycloalkyl, including (a)–(g);
n. $R_2$ is hydrogen, including (a)–(m);
o. $R_2$ is methyl, including (a)–(m);
p. A is $-CH_2CH_2-$, including (a)–(o);
q. A is cis-$CH=CH-$, including (a)–(o);
r. B is $-CH_2CH_2-$, including (a)–(q);
s. B is trans-$CH=CH-$, including (a)–(q):
t. Z is carbonyl, and X====Y is

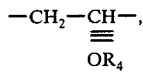

u. Z is carbonyl and X====Y is $-CH=CH-$, including (a)–(s);
v. Z is $>CH\sim\sim OR_4$ and X====Y is

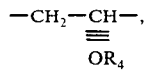

including (a)–(s); and
w. Z is $>CH\sim\sim OR_4$ and Y====Y is

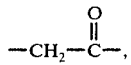

including (a)–(s).

Preferred compounds according to this invention are the following, in addition to the compounds set forth in the examples:

N-methanesulfonyl-(5Z,13E)-(8R,9S,11R,12R,15S)-9,11,15-trihydroxy-15-methyl-17-phenyl-18,19,20-trinor-prostadien-16-inic acid aminde N-methanesulfonyl-(5Z,13E)-(8R,9S,11R,12R, 15R)-9,11,15-trihydroxy-15-methyl-17-phenyl-18,19,20-trinor-prostadien-16-inic acid amide N-methanesulfonyl-(5Z,13E)-(8R,11R,12R,15S)-11,15-dihydroxy-15-methyl-9-oxo-17-phenyl-18,19,20-trinor-prostadien-16-inic acid amide.

N-methanesulfonyl-(5Z,13E)-(8R,11R,12R,15R)-11,15-dihydroxy-15-methyl-9-oxo-17-phenyl-18,19,20-trinor-prostadien-16-inic acid amide N-methanesulfonyl-(5Z,13E)-(8R,9S,11R,12R,15S)-9,11,15-trihydroxy-15-methyl-17-(4-chlorophenyl)-18,19,20-trinor-prostadien-16-inic acid amide N-methanesulfonyl-(5Z,13E)-(8R,9S,11R,12R,15R)-9,11,15-trihydroxy-15-methyl-17-(4-chlorophenyl)-18,19,20-trinor-prostadien-16-inic acid amide N-methanesulfonyl-(5Z,13E)-(8R,11R,12R15S)-11,15-dihydroxy-15-methyl-9-oxo-17-(4-chlorophenyl)-18,19,20-trinor-prostadien-16-inic acid amide N-methanesulfonyl-(5Z,13E)-(8R,11R,12R,15R)-11,15-dihydroxy-15-methyl-9-oxo-17-(4-chlorophenyl)-18,19,20-trinor-prostadien-16-inic acid amide N-methanesulfonyl-(5Z,13E)-(8R,9S,11R,12R,15S)-9,11,15-trihydroxy-17-phenyl-18,19,20-trinor-prostadien-16-inic acid amide N-methanesulfonyl-(5Z,13E)-(8R,9S,11R, 12R,15R)-9,11,15-trihydroxy-17-phenyl-18,19,20-trinor-prostadien-16-inic acid amide N-methanesulfonyl-(5Z,13E)-(8R,11R,12R,15R)-11,15-dihydroxy-9-oxo-17-phenyl-18,19,20-trinor-prostadien-16-inic acid amide N-methanesulfonyl-(5Z,13E)-(8R,11R,12R,15S)-11,15-dihydroxy-9-oxo-17-phenyl-18,19,20-trinor-prostadien-16-inic acid amide N-methanesulfonyl-(5Z,13E)-(8R,9S,11R,12R,15S)-9,11,15-trihydroxy-15-methyl-17-(3-trifluoromethylphenyl)-18,19,20-trinorprostadien-16-inic acid amide N-methanesulfonyl-(5Z,13E)-(8R,9S,11R,12R,15R)-9,11,15-trihydroxy-15-methyl-17-(3-trifluoromethylphenyl)-18,19,20-trinorprostadien-16-inic acid amide N-methanesulfonyl-(5Z,13E)-(8R,11R,12R,15S)-11,15-dihydroxy-15-methyl-9-oxo-17-(3-trifluoromethylphenyl)-18,19,20-trinorprostadien-16-inic acid amide N-methanesulfonyl-(5Z,13E)-(8R,11R,12R,15R)-11,15-dihydroxy-15-methyl-9-oxo-17-(3-trifluoromethylphenyl-18,19,20-trinorprostadien-16-inic acid amide.

Compounds of Formula II are reacted with an organometallic compound of Formula III in a conventional manner in an inert solvent or solvent mixture, e.g., diethyl ether, tetrahydrofuran, dioxane, dimethoxyethane, preferably diethyl ether. The reaction is conducted at temperatures between −100° C. and 60° C., preferably at −60° to −30° C.

The compound of Formula III required for this reaction is prepared by reacting the corresponding terminal acetylene hydrogen compound (MH) with an organometallic compound. Examples of suitable organometallic compounds are: butyllithium, methyllithium, ethyllithium, propyllithium, phenyllithium, methylmagnesium bromide, ethylamgnesium bromide, propylmagnesium bromide, butylmagnesium bromide, but preferably butyllithium and methylmagnesium bromide.

Accordingly, the residue M of general Formula III represents an alkali metal or an alkaline earth halogen group. Preferably, M is lithium or magnesium-bromine.

Reaction of lactols IV with Wittig reagent of Formula V, obtainable from the corresponding phosphonium bromide with methanesulfinylmethylsodium or potassium tert.-butylate in dimethyl sulfoxide, is conducted at temperatures of 0°–100° C., preferably 20°–80° C., in an aprotic solvent, preferably dimethyl sulfoxide or dimethylformamide. The Wittig reagent can also be liberated by reaction of 4—$R_1$—O—CO-triphenylbutylphosphonium bromide with potassium tert.-butylate.

Introduction of an ester —$OR_5$ for $R_1$ wherein $R_5$ is alkyl or 1–10 carbon atoms takes place according to the methods known to persons skilled in the art. For example, 1-carboxy compounds are conventionally reacted with diazohydrocarbons. Esterification with diazohydrocarbons is accomplished, for example, by mixing a solution of diazohydrocarbon in an inert solvent, preferably diethyl ether, with the 1-carboxy compound in the same or another inert solvent, for example, methylene chloride. After the reaction is finished (1–30 minutes), the solvent is removed and the ester purified as usual.

Diazoalkanes are either known or can be prepared according to conventional methods, e.g., Org. Reactions 8, 389–394 (1954).

To introduce an ester O—$CH_2$—U—V for $R_1$, the 1-carboxy compound of Formula I is reacted, in the presence of a hydrogen halide acceptor, with a halogen compound of the formula Hal—$CH_2$—U—V wherein Hal is a halogen atom, preferably bromine;
U is a direct bond, carbonyl, or carbonyloxy; and
V is phenyl ring substituted by one to three phenyl, alkoxy groups of 1-2 carbon atoms, or halogen, preferably bromine.

Suitable hydrogen halide acceptors are, for example, silver oxide, sodium carbonate, potassium carbonate, sodium bicarbonate, potassium bicarbonate, or amines, such as trimethylamine, triethylamine, tributylamine, trioctylamine, and pyridine. The reaction with halogen compound is conducted in an inert solvent, preferably acetone, acetonitrile, dimethylacetamide, dimethylformamide, or dimethylsulfoxide at temperatures of −80° to +100° C., preferably at room temperature.

To introduce an ester group —$OR_5$ for $R_1$ wherein $R_5$ is a substituted or unsubstituted aryl group, a 1-carboxy compound is reacted with a corresponding arylhydroxy compound with dicyclohexylcarbodiimide in the presence of a suitable base, e.g. pyridine or triethylamine, in an inert solvent. Suitable solvents include, but are not limited to, methylene chloride, ethylene chloride, chloroform, ethyl acetate, tetrahydrofuran, preferably chloroform. The reaction is effected at temperatures of between −30° and +50° C., preferably at 10° C.

Prostaglandin esters are saponified by methods known to those skilled in the art, for example, with alkaline catalysts or by reductive cleavage.

The reduction of the 9-keto group to prepare the corresponding $F_\beta$ analogs (A is > CHOH) takes place using a reducing agent suitable for the reduction of ketones, e.g., sodium or zinc borohydride. The thus-produced mixture of epimers is separated, for example, in the usual manner by column or layer chromatography.

Dehydration of a 9-oxo compound wherein the 11-hydroxy group and a hydrogen atom from the 10-position are split off, thus producing a prostaglandin A derivative, can be accomplished under conditions generally known to persons skilled in the art. In general, the dehydration is conducted in a solution of an organic acid, such as acetic acid, or an inorganic acid, such as hydrochloric acid, or in an acetic anhydride-pyridine mixture at temperatures of between 20° and 80° C. The reaction is terminated after about 2–17 hours.

The regioselective oxidation of the 9-hydroxy group (i.e., the selective oxidation of the 9-hydroxy group in the presence of another hydroxy group, e.g., the 11-hydroxy group of compounds of Formula I wherein $R_2$ is alkyl,

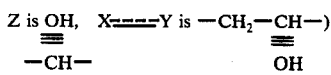

can be accomplished, for example, with silver carbonate, Fetizon reagent, Tetrahedron 29, 2867 (1973), or platinum with oxygen, Adv. in Carbohydrate Chem. 17, 169 (1962) in an inert solvent. Suitable solvents are benzene, toluene, xylene, ethyl acetate, acetone, tetrahydrofuran, diethyl ether and dioxane. The reaction temperatures are between 20° and 110° C. in the silver carbonate or Fetizon oxidation, preferably the boiling temperature of the solvent, and during the oxidation with platinum/oxygen, the temperature is preferably 20°–50° C.

The regioselective oxidation of the 11-hydroxy group (compounds of Formula I wherein $R_2$ is alkyl,

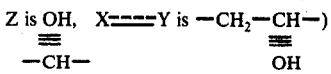

can be effected, for example, with Jones reagent, J. Chem. Soc. 1953, 2555, at −40° to +20° C., preferably at −10° to −30° C., or with the Collins reagent, Tetrahedron Letters 1968, 3363, in methylene chloride solution at −20° to 30° C., preferably at 0°–20° C. In place of methylene chloride, it is also possible to use other solvents inert with respect to the oxidizing agent, such as chloroform, ethylene chloride, pyridine, etc.

Oxidation of the 9-hydroxy group can also be accomplished, after first blocking the 11- and 15-hydroxy groups, for example, by silylation, Chem. Comm. 1972, 1120. The oxidation is accomplished with the customary oxidizing agents, e.g. with Jones reagent.

Liberation of functionally modified hydroxy group to obtain the compounds of Formula I takes place conventionally. For example, ether blocking groups are split off in an aqueous solution of an organic acid, e.g., acetic acid, propionic acid, and others, or in an aqueous solution of an inorganic acid, e.g., hydrochloric acid. To improve solubility, a water-miscible inert organic solvent is advantageously added. Suitable organic solvents are, for example, alcohols, such as methanol and ethanol; and ethers, such as dimethoxyethane, dioxane, and tetrahydrofuran. Tetrahydrofuran is preferably employed. The cleavage is preferably carried out at temperatures between 20° and 80° C. In case of compounds of the prostaglandin E type, the hydrolysis is conducted below 45° C. to avoid formation of prostaglandin A compounds as by-products.

The acyl groups are saponified, for example, with alkali or alkaline earth carbonates or hydroxides in an alcohol or the aqueous solution of an alcohol. Suitable alcohols are aliphatic alcohols, for example, methanol, ethanol, butanol, etc., preferably methanol. Suitable alkali carbonates and hydroxides are potassium and sodium salts, but potassium salts are preferred. Examples of suitable alkaline earth carbonates and hydroxides are calcium carbonate, calcium hydroxide, and barium carbonate. The reaction takes place at $-10°$ to $70°$ C., preferably at 25° C.

Functional modification of the free OH-groups takes place according to known methods. To introduce an ether blocking group, the reaction is conducted, for example, with dihydropyran in methylene chloride or chloroform using an acidic condensation agent, for example, p-toluenesulfonic acid. Dihydropyran is used in excess, preferably 4–10 times the theoretical quantity required. The reaction is normally complete after 15–30 minutes at 0° to 30° C.

Acyl blocking groups are introduced by conventionally reacting a compound of Formula I with a carboxylic acid derivative, e.g., an acid chloride or acid anhydride.

Prostaglandin derivatives of Formula I can be converted to salts by neutralization with suitable amounts of the corresponding inorganic bases. For example, when corresponding PG acids are dissolved in water containing the stoichiometric quantity of base, solid inorganic salt is obtained after evaporation of water or after adding a water-miscible solvent, e.g., alcohol or acetone.

To prepare an amine salt, which is accomplished in the usual manner, the PG acid is dissolved, for example, in ethanol, acetone, diethyl ether, or benzene, and at least the stoichiometric amount of amine is added to this solution. In this procedure, the salt is ordinarily obtained in the solid form or is isolated in the usual way after evaporation of the solvent.

Racemates are separated by conventional methods, such as salt formation with an optically active base, e.g., dihydroabietylamine, amphetamine, and quinine.

Compounds of Formula II serving as the starting compounds can be prepared by reacting in a conventional Wittig reaction, an aldehyde of Formula VI, E. J. Corey et al, J. Amer. Chem. Soc. 91, 5675 (1969); E. W. Yankee et al, J. Amer. Chem. Soc. 96, 5865 (1974)

VI

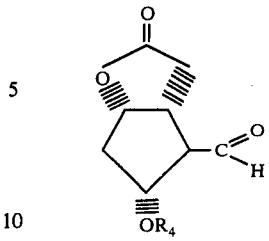

wherein $R_4$ is as above,
with a phosphorane or phosphonate. In this way, an $\alpha,\beta$-unsaturated carbonyl compound is obtained, the double bond of which can, if desired, be hydrogenated in the 13,14-position (PG numbering). The carbonyl group is ketalized and the lactone is thereafter reduced to the lactol with diisobutyl aluminum hydride. The lactol is reacted with a Wittig reagent to obtain compounds of Formula VII

VII

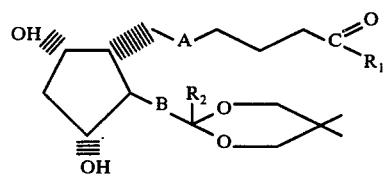

wherein $R_1$, $R_2$, A, and B are as above.
Optionally, the 5,6-double bond (PG numbering) is hydrogenated and/or the 1-carboxy group is esterified. Subsequent hydrolysis of ketals of Formula VII leads to starting compounds of Formula II wherein hydroxy groups in the 9- and 11-positions are optionally etherified or esterified. The esterification of the hydroxy groups in the 9- and 11-positions takes place under the conditions known to those skilled in the art, for example, with an acid chloride or acid anhydride in pyridine.

Another way of obtaining the starting compounds of Formula II is the conventional reaction of an aldehyde of Formula VI with the triethyl ester of orthoformic acid and ethanol in the presence of an acidic catalyst to obtain the acetal, which is reduced thereafter with diisobutyl aluminum hydride to the lactol. The lactol is reacted with a Wittig reagent of Formula V to produce compounds of Formula VIII

VIII

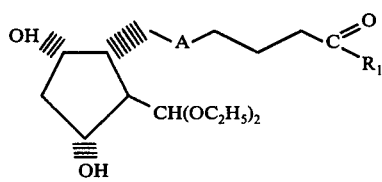

wherein $R_1$ and A are as above,
optionally after hydrogenation of the 5,6-double bond (PG numbering) and/or esterification of the 1-carboxy group.

After blocking the hydroxy group in the 9- and 11-positions, the acetal of Formula VIII is hydrolyzed to the aldehyde. The thus-obtained aldehyde is reacted with a phosphorane or a phosphonate in a Wittig reaction to the starting compound of Formula II, the hydroxy groups in the 9- and 11-positions of which are optionally etherified or esterified and/or the 13,14-double bond (PG numbering) of which is optionally hydrogenated.

The lactol of Formula IV used as starting material can be produced by reacting, in a Wittig reaction, an aldehyde of Formula VI with a phosphorane or phosphonate to obtain an α,β unsaturated carbonyl compound, the double bond of which can optionally be hydrogenated in the 13,14-position (PG numbering). The reaction of a carbonyl compound with an organometallic compound of Formula III leads to epimeric $C_{15}$-alcohols (PG numbering), the epimers of which are readily separable by conventional methods. The reaction is conducted in an inert solvent or solvent mixture at temperatures of between $-100°$ and $60°$ C., preferably at $-60°$ to $-30°$ C. Subsequently, blocking groups can be introduced, if desired. The thus-obtained lactone is reduced with diisobutyl aluminum hydride to the lactol of Formula IV.

The novel prostanoic acid derivatives of Formula I are valuable pharmacological agents, since they exhibit, with a similar spectrum of effectivenss, a substantially stronger and above all, longer activity than the corresponding natural prostaglandins.

The novel prostaglandin analogs of the E-, D- and F-type have a very strong luteolytic effect, i.e., for triggering luteolysis substantially lower dosages are required than in case of the corresponding natural prostaglandins.

For triggering abortions, essentially lower quantities of the novel prostaglandin analogs are required as compared to the natural prostaglandins. Investigations were conducted on gravid rats and guinea pigs by the usual methods. Gravid rats were treated from the 4th to the 7th day of pregnancy subcutaneously with the compounds of this invention. On the 9th day, the animals were sacrificed and the uteri examined for points of implantation. It was found that, for example, the methyl ester of (5Z,13E)-(8R,9S,11R,12R,15S)-9,11,15-trihydroxy-20-ethyl-15-methyl-prostadien-16-inic acid shows, at a tenfold lower dosage, an abortive effect as good as $PGF_{2\alpha}$. Likewise, for example, the methyl ester of (5Z,13E)-(8R,11R,12R,15R)-11,15-dihydroxy-15-methyl-9-oxo-prostadien-16-inic acid is, compared to 1 mg. of $PGE_2$ per animal, as effective for triggering an abortion in a dosage which is 30 times smaller.

In the recording of isotonic uterus contraction of narcotized rats and of isolated rat uterus, compounds of this invention are essentially more effective and their activities are of a longer duration than those of natural prostaglandins.

The novel prostynoic acid derivatives are suitable to induce menstruation or interrupt a pregnancy after a single intrauterine administration. They are furthermore suitable for synchronizing the sexual cycle in female mammals, such as monkeys, rabbits, cattle, pigs, etc.

The good dissociation of effectiveness in the compounds of this invention is shown in the investigation on other smooth muscle organs, for example, on guinea pig ileum or isolated rabbit trachea, where a substantially lesser stimulation is observed than caused by the natural prostaglandins.

The effective agents of this invention of the PGE series show, on isolated rabbit trachea in vitro, a bronchodilatory effect and strongly inhibit stomach acid secretion. They also have a regulating action in cardiac dysrhythmia. Novel compounds of the PGA and PGE series lower blood pressure and have a diuretic effect.

Active agents of this invention related to the F series have a lower bronchoconstrictive effect than natural prostaglandin $F_{2\alpha}$, which is of great advantage in their therapeutic usage. For medical application, the effective agents can be converted into a form suitable for inhalation, oral or parenteral administration. For purposes of inhalation, aerosol or spray solutions are advantageously prepared. Sprayable aerosol preparations are those wherein the active ingredient, preferably in combination with a solid or liquid inert carrier material, is packaged in a squeeze bottle or in admixture with a pressurized volatile, normally gaseous propellant, e.g., a freon.

Suitable for oral application are, for example, tablets, dragees, or capsules.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The invention accordingly also relates to medicinal agents on the basis of the compounds of Formula I and customary auxiliary agents and carriers.

The compounds of this invention are thus employed in mixture with conventional excipients, i.e., pharmaceutically acceptable organic or inorganic carrier substancies suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

The effective agents of this invention are used, in conjuction with the auxiliary agents known and customary in galenic pharmacy, for example, in preparations to trigger abortion, for cycle control, or to induce labor. For this purpose, sterile, aqueous solutions containing 0.01-19 μg./ml. of the active compound can be used as an intravenous infusion. For the preparation of aqueous, isotonic solutions, acids and salts of Formula I are especially well suited. To increase solubility, alcohols, such as ethanol, ethylene glycol, and propylene glycol, can be added.

In the specification and claims the designation "16-inic acid" represents a prostaglandin compound with a triple bond between $C_{16}$–$C_{17}$. Alternatively, these compounds may be named "16-ynoic acid".

In the following Examples, the temperatures are set forth in degrees Celsius.

Without further elaboration, it is believed that one skilled in the art can, using the preceding description,

EXAMPLE 1

Methyl Ester of (5Z, 13E) -
(8R,9S,11R,12R,15S)-9,11,15-Trihydroxy-15-methyl-prostadien-16-inic Acid and Methyl Ester of
(5Z,13E)-(8R,9S,11R,12R,15R)-9,11,-15-Trihydroxy-15-methyl-prostadien-16-inic Acid A solution of 1.30 g. of the methyl ester of (5Z,13E)-(8R,9S,11R,12R,15RS)-9,11-bis(benzoyloxy)-15-hydroxy-15-methylprostadien-16-inic acid in 55 ml. of absolute methanol was combined with 1.23 g. of anhydrous potassium carbonate and stirred for 15 hours at room temperature under argon. After dilution with 300 ml. of ether, the mixture was shaken three times with respectively 50 ml. of water, dried over magnesium sulfate, and evaporated under vacuum. After chromatographing the residue on silica gel (deactivated with 3% water), 260 mg. of the 15S(15 β)-configured title compound was obtained with ether/ethyl acetate (9+1) in the form of a colorless oil, and as the more polar component, 290 mg. of the 15R(15 α)-configured title compound was produced as colorless crystals, m.p. 58° C.

TLC (ether):
(15S) Rf value 0.19
(15R) Rf value 0.12

IR (15S): 3600, 3450 (wide), 2995, 2960, 2938, 2878, 2240, 1728, 1600, 1438, 970 cm$^1$.
IR (15R): 3600, 3450 (wide), 2995, 2960, 2938, 2878, 2240, 1728, 1600, 1438, 970 cm$^1$.

The spectrum is congruent with that of the 15S-compound.

NMR (DMSO-d$_6$)
(15R)-epimer:
δ: 5.2–5.7 (4H,m); 4.50 (1H,d, J=5Hz); 4.33 (1H,d, J=5Hz); 3.61 (3H,s); 2.20 (2H,t, J=7Hz); 1.38 (3H,s); 0.95 (3H,t, J=7Hz).

(15S)-epimer:
δ: 5.2–5.7 (4H,m); 4.53 (1H,d J=5Hz); 4.33 (1H,d, J=5Hz); 3,60 (3H,s); 2.19 (2H,t, J=7Hz); 1.38 (3H,s); 0.95 (3H,t, J=7Hz).

The starting material for the above compounds was prepared as follows:

1(a) Dimethylacetonylphosphonate

At 50°–65°, 72.1 g. of trimethylphosphite was added dropwise to a solution of 109.6 g. of iodoacetone in 75 ml. of benzene; the thus-formed methyl iodide was distilled off continuously. The mixture was then heated for one hour under reflux, thus obtaining after distillation at 15 torr (mm. Hg) and at 128°–135° 55 g. of dimethylacetonylphosphonate as a clear, colorless liquid.

1(b) (1S,5R,6R,7R)-6-[(E)-3-Oxo-1-butenyl]-7-benzoyloxy-2-oxabicyclo[3,3,0]octan-3-one At 20° under argon, a solution of 5.1 g. of dimethylacetonylphosphonate in 30 ml. of dimethoxyethane was added dropwise to a mixture of 1.46 g. of sodium hydride suspension (50%) in mineral oil and 175 ml. of dimethoxyethane. To this mixture was added 1.3 g. of lithium chloride and the mixture was agitated for two hours, whereafter a solution of 8.3 g of (1S,5R,6R,7R)-6-formyl-7-benzoyloxy-2-oxabicyclo[3,3,0]octan-3-one J. Amer. Chem. Soc. 96, 5865 (1974) in 60 ml. of tetrahydrofuran was added thereto dropwise at −10°. The mixture was then stirred for 2 hours at −10°. After neutralization with glacial acetic acid, the mixture was combined with water, extracted with ether, the ether phase extracted with sodium bicarbonate solution and water, dried over magnesium sulfate, and evaporated under vacuum. Chromatography of the residue on silica gel yielded, with ether, 6.80 g. of the title compound as colorless crystals, m.p. 62°–63°.

1(c) (1S,5R,6R,7R)-6-[(E)-3,3-(2,2-Dimethyltrimethylenedioxy)-1-butenyl]-7-benzoyloxy-2-oxabicyclo[3,3,0]octan-3-one 1.50 g. of the ketone produced according to 1(b), 0.9 g. of 2,2-dimethylpropane-1,3-diol, 15 mg. of p-toluenesulfonic acid in 60 ml. of benzene were heated for 1 hour under reflux with the use of a water trap. After cooling, the mixture was diluted with ether and shaken in succession with saturated sodium bicarbonate solution and brine, dried over magnesium sulfate, and evaporated under vacuum. Filtration over silica gel with ether/hexane mixtures and recrystallization from methylene chloride/isopropyl ether yielded 1.3 g. of colorless crystals of the title compound, m.p. 132°.

1(d) (2RS,3aR,4R,5R,6aS)-4-[(E)-3,3-(2,2-Dimethyltrimethylenedioxy)-1-butenyl]-2,5-dihydroxyperhydrocylclopenta[b]furan Under argon, 85 ml. of a 20% solution of diisobutyl aluminum hydride in toluene was added dropwise to a solution of 8.50 g. of the compound prepared as described in 1(c) in 450 ml. of toluene, cooled to −60°. The mixture was agitated for 30 minutes at −60° and the reaction was then terminated by the dropwise addition of isopropanol. Thereafter, the mixture was combined with 42 ml. of water, agitated for 2 hours at +10°, diluted with methylene chloride, and filtered off from the sediment. After filtration of the residue from the evaporation over a small amount of silica gel, 6.1 g. (97.6% of theory) of the title compound was obtained with ether as colorless crystals, m.p. 119°.

1(e) (5Z,13E)-(8R,9S,11R,12R)-9,11-Dihydroxy-15,15-[2,2-dimethyl)-trimethylenedioxy]-17,18,19,20-tetranor-prostadienoic Acid Methyl Ester A solution of 53.5 g. of 4-carboxybutyltriphenylphosphonium bromide in 200 ml. of dimethyl sulfoxide was combined dropwise with 212 ml. of a solution of methanesulfinylmethylsodium in dimethyl sulfoxide (DMSO) (prepared by dissolving 10.6 g. of 50% sodium hydride suspension in 212 ml. of DMSO during one hour at 70–75°). The mixture was stirred for 30 minutes at room temperature. This red ylene solution was added dropwise to a solution of 6.0 g. of the lactol obtained according to 1(d) in 100 ml. of DMSO, and the mixture was agitated for 2 hours at 50°. Thereafter, the DMSO was exhaustively distilled off under vacuum, and the mixture was combined with b 250 ml. of ice water and extracted three times with ether. This ether extract was discarded. The aqueous phase was acidified to pH 5 with 10% citric acid solution and extracted four times with a mixture of hexane/ether (1+2). The organic phase was shaken with brine, dried over magnesium sulfate, and evaporated under vacuum, thus obtaining 12 g. of a crude product which was esterfied without any further purification in 200 ml. of methylene chloride with 80 ml. of an ethereal diazomethane solution (see "Organikum" p. 528). After chromatographing the residue from the evaporation on silica gel, 6.80 g. of the title compound was produced with ether, in the form of a colorless oil.

TLC (ether/dioxane 9+1) Rf value 0.49p2 IR (in chloroform): 3600, 2950, 1730, 970 cm[31] [1] NMR (in DMSO-$d_6$)

δ: 0.7 (3H,s); 1.10 (3h,s); 1.3 (3H,s); 2.20 (2H,t); 3.60 (3H,s); 5.2-5.75 (4H,m).

1(f) (5Z,13E)-(8R,9S,11R,12R)-9,11-Dihydroxy-15-oxo-17,18,19,20-tetranor-prostadienoic Acid Methyl Ester 6.2 g. of the compound prepared according to Example 1(e) was agitated for 4 hours at 50° in 100 ml. of a mixture of glacial acetic acid/water/tetrahydrofuran (65/35/10). The mixture was then evaporated under vacuum, the reisdue taken up in ether, shaken in succession with sodium bicarbonate solution and water, dried over magnesium sulfate, and evaporated under vacuum. Filtration over silica gel yielded, with ether/ethyl acetate (8+2), 4.5 g. of the title compound as a colorless oil.

TLC (ether/dioxane 9+1) Rf value 0.28
IR (in chloroform): 3600, 3450, 2955, 1725, 1692, 1670, 1623, 978 cm$^{-1}$.

1(g) (5Z,13E)-(8R,9S,11R,12R)-9,11-Bis(benzoyloxy)-15-oxo-17,18,19,20-tetranor-prostadienoic Acid Methyl Ester A solution of 4.50 g. of the ketone produced according to Example 1(f) and 20 ml. of pyridine was combined with 9 ml. of benzoyl chloride and allowed to stand for 16 hours at room temperature. The mixture was then combined with ice water, stirred for 2 hours at room temperature, extracted with ether, and the ether extract was shaken in succession with 10% sulfuric acid, 5% sodium bicarbonate solution, and water. The mixture was dried over magnesium sulfate and evaporated under vacuum. After filtration over silica gel, 4.26 g. of the title compound was obtained as a colorless oil with ether/hexane (8+2).

TLC (ether/hexane 7+3) Rf value 0.18
IR (in chloroform): 3030, 3000, 2955, 1715, 1672, 1625, 1600, 1583, 1589, 1450, 1265, 1024, 978 cm$^{-1}$.

1(h) (5Z,13E)-(8R,9S,11R,12R,15RS)-9,11-Bis(benzoyloxy)-15-hydroxy-15-methyl-prostadien-16-inic Acid Methyl Ester.

At −70° under argon, 26 ml. of a lithium pentyne solution (prepared by adding dropwise, at −70°, 5 ml. of an approximately 2-molar butyllithium solution in hexane to a solution of 788 mg. of 1-pentyne in 21 ml. of absolute tetrahydrofuran and agitating the mixture for 10 minutes at −70°) was added dropwise to a solution of 1.68 g. of the ketone produced according to Example 1(g) in 50 ml. of absolute ether and 40 ml. of absolute tetrahydrofuran. The mixture was agitated for 30 minutes at −70°, combined with 60 ml. of saturated ammonium chloride solution, and extracted three times with respectively 100 ml. of ether. The combined ether extracts were shaken with 50 ml. of saturated NaCl solution, dried over magnesium sulfate, and evaporated to dryness under vacuum. Column chromatography on silica gel (deactivated with 3% water) with ether/hexane (7+3) yielded 1.30 g. of the title compound (mixture of epimers) as a colorless oil.

TLC (ether): Rf value 0.57
IR: 3600, 3030, 2995, 2955, 2240, 1717, 1600, 1265, 978 cm$^{-1}$.
NMR (in DMSO-$d_6$)
δ: 7.2-8.1 (15H,m); 5.1-5.9 (6H,m); 3.48 (3H,s); 1.35 (3H,s); 0.86 (3H,t, J=7Hz).

EXAMPLE 2

Methyl Ester of (5Z,13E)-(8R,9S,11R,12R,15R)-9,11,15-Trihydroxy-prostadien-16-inic Acid and Methyl Ester of (5Z,13E)-(8R,9S,11R,12R,15S)-9,11,15-Trihydroxy-prostadien-16-inic Acid A solution of 2.10 g. of (5Z,13E)-(8R,9S,11R,12R,15RS)-9,11-diacetoxy-15-hydroxy-prostadien-16-inic acid methyl ester in 80 ml. of absolute methanol was combined with 1.30 g. of anhydrous potassium carbonate, and the mixture was agitated for 16 hours at room temperature under argon. The mixture was then diluted with 300 ml. of ether, shaken three times with respectively 50 ml. of water, dried over magnesium sulfate, and evaporated under vacuum. Column chromatography on silica gel (deactivated with 3% water) was used to separate the two 15S- and 15R-epimers with ether, thus obtaining 690 mg. of the 15S[15β-OH]-configured title compound and, as the more polar component, 675 mg. of the 15R(15α-OH)-configured title compound as colorless oils.

TLC (ether):
(15S) Rf value 0.15
(15R) Rf value 0.10
IR (15S): 3600, 3450 (wide), 2995, 2960, 2940, 2880, 2240, 1728, 1600, 1440, 975 cm$^{-1}$.
IR (15R): 3600, 3450 (wide), 2995, 2960, 2940, 2880, 2240, 1728, 1600, 1440, 975 cm$^{-1}$.

The starting material for the above compounds was prepared as follows:

2(a)
(1S,5R,6R,7R)-6-Diethoxymethyl-7-benzoyloxy-2-oxabicyclo[3,3,0]octan-3-one 8.60 g. of (1S,5R,6R,7R)-6-formyl-7-benzoyloxy-2-oxabicyclo[3,3,0]octan-3-one, J. Amer. Chem. Soc. 96, 5865 (1974), 33 ml. of triethyl orthoformate, and 95 mg. of p-toluenesulfonic acid in 33 ml. of absolute ethyl alcohol were agitated for 1.5 hours at 20° under argon, then diluted with ether, shaken in succession with sodium bicarbonate solution and water, dried over magnesium sulfate, and evaporated under vacuum, thus obtaining 10.8 g. of the title compound as an oil which was completely uniform as determined by thin-layer chromatography.

TLC (ether): Rf value 0.74
IR (in chloroform): 2975, 2930, 2880, 1765, 1712, 1601, 1583, 1450, 1275 cm$^{-1}$.

2(b)
(2RS,3aR,4R,5R,6aS)-4-Diethoxymethylperhydrocyclopenta[b]furan-2,5-diol

Under argon, 112 ml. of a 20% solution of diisobutyl aluminum hydride in toluene was added dropwise to a solution of 11.2 g. of the compound obtained according to 2(a) in 300 ml. of toluene, cooled to −60°. The mixture was stirred for 30 minutes at −60° and the reaction was terminated by the dropwise addition of 10 ml. of isopropanol. Thereafter, the mixture was combined with 56 ml. of water, allowed to warm up to room temperature, agitated for another 30 minutes, diluted with methylene chloride, and filtered off from the precipitate. After filtering the residue of the evaporation over silica gel, 6.63 g. of the title compound was obtained with ether as a colorless oil.

TLC (ether) Rf value 0.16

IR (in chloroform): 3600, 3400 (wide), 2978, 2935, 2878, 1115, 1055, 1000 cm$^{-1}$.

2(c)
(5Z)-(8R,9S,11R,12R)-9,11-Dihydroxy-13,13-diethoxy-14,15,16,17,18,19,20-heptanorprostenoic Acid Methyl Ester 230 ml. of a solution of methanesulfinylmethylsodium in DMSO (preparation: see Example 1[c]) was added dropwise to a solution of 53.5 g. of 4-carboxybutyltriphenylphosphonium bromide in 170 ml. of DMSO; the mixture was stirred at room temperature under argon for 30 minutes. The red ylene solution was added dropwise to a solution of 6.6 g. of the lactol obtained according to 2(b) in 60 ml. of DMSO, and the mixture was agitated for 2 hours at 48° and then poured onto ice water. The mixture was extracted three times with ether, and this ether extract was discarded. The aqueous phase was acidified with 10% citric acid solution to pH 5 and extracted five times with a mixture of ether/hexane (2+1). This organic extract was shaken with brine, dried over magnesium sulfate, and evaporated under vacuum, thus obtaining 12.4 g. of a crude product which was esterified, without further purification, in 200 ml. of methylene chloride with 140 ml. of an ethereal diazomethane solution (see "Organikum" p. 528). After chromatography of the evaporation residue on silica gel, 6.25 g. of the title compound was produced with ether as a colorless oil.

TLC (ether): Rf value 0.39

IR: 3600, 3520 (wide), 2975, 2930, 2875, 1730, 1600, 1055, 1005 cm$^{-1}$.

2(d)
(5Z)-(8R,9S,11R,12R)-9,11-Bis(acetoxy)-13,13-diethoxy-14,15,16,17,18,19,20-heptanorprostenoic Acid Methyl Ester 2 g. of the diol obtained according to 2(c) in 4 ml. of pyridine was combined with 2 ml. of acetic anhydride and allowed to stand for 20 hours at room temperature. The mixture was then combined with water, extracted with ether, the organic extract was shaken in succession with 5% sulfuric acid, 5% sodium bicarbonate solution, and water, dried over magnesium sulfate, and evaporated under vacuum, thus obtaining 2.30 g. of the title compound, which was completely uniform as determined by thin-layer chromatography, in the form of a colorless oil.

TLC (ether): Rf value 0.87

NMR (in DMSO-d$_6$)

δ: 1.12 (3H,t); 1.15 (3H,t); 1.99 (3H,s); 2.02 (3H,s); 3.60 (3H,s); 4.52 (1H,d); 4.85-5.07 (2H,m); 5.23-5.42 (2H,m).

2(e)
(5Z)-(8R,9S,11R,12R)-9,11-Bis(acetoxy)-12-formyl-13,14,15,16,17,18,19,20-octanorprostenoic Acid Methyl Ester 2.20 g. of the compound prepared according to Example 2(d) was agitated for 16 hours at room temperature in 40 ml. of a mixture of glacial acetic acid/water/tetrahydrofuran (65/35/10) and evaporated to dryness under vacuum, thus obtaining 2.05 g. of the title compound, which was uniform as determined by thin-layer chromatography, as a light-yellow oil.

TLC (ether): Rf value 0.71

IR: 2958, 2730, 1730 (wide), 1245 cm$^{-1}$.

2(f),
(5Z,13E)-(8R,9S,11R,12R)-9,11-Bis(acetoxy)-15-oxo-16,17,18,19,20-pentanor-prostadienoic Acid Methyl Ester A mixture of 2.0 g. of the aldehyde obtained according to Example 2(e), 1.72 g. of formylmethylenetriphenylphosphorane (J. Chem. Soc. 1961, 2130), 20 mg. of benzoic acid, and 50 ml. of benzene was agitated for 48 hours at room temperature under argon. Chromatography of the evaporation residue on silica gel with ether/hexane (8+2) yielded 980 mg. of the title compound as a colorless oil.

TLC (ether): Rf value 0.42

IR: 2955, 2855, 2740, 1730, 1687, 1640, 1435, 1375, 1240, 970 cm$^{-1}$.

NMR (in CDCl$_3$)

δ: 2.08 (3H,s); 2.13 (3H,s); 3.66 (3H,s); 4.8-5.5 (4H,m); 6.15 (1H, J=15+7Hz, dd); 6.75 (1H, J=15+7Hz, dd); 9.54 (1H, J=7Hz, d).

2(g)
(5Z,13E)-(8R,9S,11R,12R,15RS)-9,11-Bis(acetoxy)-15-hydroxy-prostadien-16-inic Acid Methyl Ester At −70°, under argon, 60 ml. of a lithium pentyne solution was added dropwise to a solution of 1.90 g. of the compound obtained according to Example 2(f) in 150 ml. of tetrahydrofuran (absolute) and 100 ml. of ether (absolute). The mixture was stirred for 60 minutes at −70°, combined with 100 ml. of saturated ammonium chloride solution, allowed to warm up to room temperature, extracted three times with respectively 100 ml. of ether, and the organic phase was shaken twice with respectively 60 ml. of water. The mixture was dried over sodium sulfate and evaporated under vacuum. After chromatography on silica gel (deactivated with 3% water) 1.40 g. of the title compound was obtained with hexane/ether (6+4) in the form of a colorless oil.

TLC (ether): Rf value 0.47

IR: 3580, 3030, 2998, 2955, 2238, 1730, 978 cm$^{-1}$.

EXAMPLE 3
(5Z,13E)-(8R,9S,11R,12R,15R)-9,11,15-Trihydroxy-18,18-dimethyl-20-nor-prostadien-16-inic Acid 260 mg. of (5Z,13E)-(8R,9S,11R,15R)-11,15-bis(tetrahydropyranyloxy)-9-hydroxy-18,18-dimethyl-20-nor-prostadien-16-inic acid was agitated in 9 ml. of a mixture of acetic acid/water/tetrahydrofuran (65/35/10) for 3 hours at 25° and then evaporated under vacuum. Column chromatography on 15 g. of silica gel with chloroform/ethanol (4+1) yielded 120 mg. of the title compound as a colorless oil.

TLC (benzene/dioxane/glacial acetic acid 20/20/1):

Rf value 0.27
IR: 3600, 3300 (wide), 3000, 2940, 2235, 1710 (wide), 970 cm$^{-1}$.

The starting material for the above title compound was produced as follows:

3(a)
(1S,5R,6R,7R)-6-[(E)-Prop-1-en-3-al-1-yl]-7-benzoyloxy-2-oxabicyclo[3,3,0]octan-3-one A mixture of 3 g. of (1S,5R,6R,7R)-6-formyl-7-benzoyloxy-2-oxabicyclo[3,3,0]octan-3-one, 3.9 g. of formylmethylenetriphenylphosphorane, 50 ml. of benzene, and 20 ml. of methylene chloride was agitated for 48 hours at room temperature under argon. Chromatography of the residue from the evaporation on silica gel with ether/hexane (8+2) yielded 2.05 g. of the title compound as a yellowish oil.

TLC (ether): Rf value 0.35
IR: 2950, 2740, 1765, 1710, 1690, 1640, 975 cm$^{-1}$.

3(b)
(1S,5R,6R,7R)-6-[(E)-(3R)-6,6-Dimethyl-3-hydroxyhept-1-en-4-yn-1-yl]-7-benzoyloxy-2-oxabicyclo[3,3,0]octan-3-one and
(1S,5R,6R,7R)-6-[(E)-(3S)-6,6-Dimethyl-3-hydroxyhept-1en-4-yn-1-yl]-7-benzoyloxy-2-oxabicyclo[3,3,0]octan-3-one At −70° under argon, 70 ml. of a lithium tert.-butylacetylide solution (prepared by adding dropwise at −70° under argon 10.5 ml. of an approximately 2-molar butyllithium solution in hexane to a solution of 1.70 g. of tert.-butylacetylene in 50 ml. of absolute tetrahydrofuran and stirring the mixture for 10 minutes at −70°) was added dropwise to a solution of 6 g. of the compound obtained in accordance with Example 3(a) in 150 ml. of absolute tetrahydrofuran and 150 ml. of absolute ether. The mixture was agitated for 30 minutes at −70°, mixed with 150 ml. of saturated ammonium chloride solution, allowed to warm up to room temperature, extracted three times with respectively 150 ml. of ether, and the organic phase was shaken twice with respectively 80 ml. of water. The mixture was dried over magnesium sulfate and evaporated under vacuum. Chromatography on silica gel with ether/hexane (8+2) yielded, first of all, 1.80 g. of the 15R-(corresponding to 15 α-hydroxy) title compound and, as the more polar component, 1.91 g. of the 15S-(corresponding to 15β-hydroxy) title compound (according to prostaglandin numbering) as colorless oils.

TLC (ether):
(15R) Rf value 0.26
(15S) Rf value 0.24
IR (chloroform):
(15R): 3600, 2985, 2938, 2240, 1770, 1715, 1603, 1585, 973 cm$^{-1}$.
(15S): 3600, 2987, 2940, 2240, 1770, 1715, 1603, 1585, 973 cm$^{-1}$.

3(c)
(1S,5R,6R,7R)-6-[(E)-(3R)6,6-Dimethyl-3-hydroxyhept-1-en-4-yn-1-yl]-7-hydroxy-2-oxabicyclo[3,3,0]octan-3-one 290 mg. of anhydrous potassium carbonate was added to a solution of 780 mg. of the α-alcohol obtained according to Example 3(b) in 40 ml. of absolute methanol. The mixture was stirred for 3 hours at room temperature under argon. Then, 40 ml. of 0.1N hydrochloric acid was added thereto and the mixture was diluted with 150 ml. of saturated NaCl solution, extracted three times with respectively 100 ml. of ethyl acetate, shaken twice with respectively 50 ml. of saturated NaCl solution, dried over magnesium sulfate, and evaporated under vacuum. The residue was chromatographed on silica gel (ether/ethyl acetate 7+3), thus obtaining 510 mg. of the title compound as a colorless oil.

TLC (ether/dioxane 9+1): Rf value 0.26
IR: 3600, 3300, 2998, 2238, 1770, 978 cm$^{-1}$.

3(d)
(1S,5R,6R,7R)-6-[(E)-(3R)-6,6-Dimethyl-3-(tetrahydropyran-2-yloxy)-hept-1-en-4-yn-1-yl]-7-(tetrahydropyran-2-yloxy)-2-oxabicyclo[3,3,0]-octan-3-one 480 mg. of the compound produced according to Example 3(c), 120 ml. of freshly distilled dihydropyran, 20 mg. of p-toluenesulfonic acid in 15 ml. of absolute methylene chloride were agitated for 30 minutes at 5° under argon. After dilution with 150 ml. of methylene chloride, the mixture was shaken with 30 ml. of saturated sodium bicarbonate solution and then twice with 50 ml. portions of water, dried over magnesium sulfate, and evaporated to dryness under vacuum. Filtration of the residue over silica gel with ether/hexane (7+3) yielded 505 mg. of the title compound as a colorless oil.

TLC (ether): Rf value 0.52
IR: 2998, 2238, 1770, 978 cm$^{-1}$.

3(e) (2RS, 3aR, 4R,6aS)-4-[(E)-(3R)-6,6-Dimethyl-3-(tetrahydropyran-2-yloxy)-hept-1-en-4-yn-1-yl]-7-tetrahydropyran-2-yloxy)-perhydrocyclopenta[b]furan-2-ol Under argon, 5 ml. of a 20% solution of diisobutyl aluminum hydride in toluene was added dropwise to a solution of 500 mg. of the bis(tetrahydropyranyl ether) prepared in accordance with Example 3(d) in 30 ml. of toluene, cooled to −60°. The mixture was stirred for 30 minutes at −60°, the excess reagent was decomposed by the dropwise addition of isopropyl alcohol. Then, 2.5 ml. of water was added to the mixture and the latter was allowed to warm up to room temperature, then stirred for 30 minutes, diluted with 50 ml. of methylene chloride, and filtered off from the precipitate. Evaporation yielded 497 mg. of the title compound as a colorless oil.

TLC (ether): Rf value 0.31
IR (in chloroform): 3600, 3400 (wide), 2985, 2240, 978 cm$^{-1}$.

3(f)
(5Z,13E)-(8R,9S,11R,12R,15R)-11,15-Bis(tetrahydropyran-2-yloxy)-9-hydroxy-18,18-dimethyl-20-nor-prostadien-16-inic Acid At 20°, 8 ml. of a solution of methanesulfinylmethylsodium in absolute DMSO (prepared by dissolving 385 mg. of 50% sodium hydride suspension in 8 ml. of DMSO at 75° during the course of one hour) was added to a solution of 1.77 g. of 4-carboxybutyltriphenylphosphonium bromide in 7 ml. of DMSO. The mixture was stirred for 30 minutes at 20°. To this solution was added dropwise 448 mg. of the lactol obtained according to Example 3(e), dissolved in 7 ml. of DMSO, and the mixture was agitated for 2 hours at 50°. The mixture ws then poured on ice water and extracted three times with ether. This ether extract was discarded. The aqueous phase was acidified to pH 4 with 10% aqueous citric acid solution and extracted four times with respectively 60 ml. of an ether/hexane mixture (1+1). The organic phase was shaken with 50 ml. of brine, dried over magnesium sulfate, and evaporated under vacuum. After chromatography on silica gel with ether, 390 mg. of the title compound was obtained as a colorless oil.

TLC (chloroform/tetrahydrofuran/acetic acid 10/2/1): Rf value 0.55

IR (chloroform): 3600, 3300 (wide), 2989, 2940, 2240, 1710 (wide), 970 cm$^{-1}$.

EXAMPLE 4

(5Z,13E)-(8R,9S,11R,12R,15S)-9,11,15-Trihydroxy-15,20-dimethylprostadien-16-inic Acid Methyl Ester and (5Z,13E)-(8R,9S,11R,12R,15R)-9,11,15-Trihdroxy-15,20-dimethylprostadien-16-inic Acid Methyl Ester A solution of 3.95 g. of (5Z,13E)-(8R,9S,11R,12R,15RS)-9,11-bis(benzoyloxy)-15-hydroxy-15,20-dimethyl-prostadien-16-inic acid methyl ester in 170 ml. of absolute methanol was combined with 3.70 g. of anhydrous potassium carbonate. The mixture was agitated for 16 hours at room temperature under argon. After dilution with 1000 ml. of ether, the mixture was shaken three times with respectively 100 ml. of water, dried over magnesium sulfate, and evaporated under vacuum. After chromatography of the residue on silica gel (deactivated with 3% water), 930 mg. of the 15S(15β)-configured title compound was obtained with ether/ethyl acetate (95+5), and, as the more polar component, 945 mg. of the 15R(15α)-configurated title compound was also obtained both in the form of colorless oils.

TLC (ether):
 (15S) Rf value 0.23
 (15R) Rf value 0.17

IR (15S): 3600, 3450 (wide), 2990, 2960, 2940, 2238, 1730, 1600, 1438, 970 cm$^{-1}$.

The IR spectrum of the 15R-compound is almost congruent.

The starting material for the above compounds was prepared as follows:

4(a)

(5Z,13E)-(8R,9S,11R,12R,15RS)-9,11-Bis(benzoyloxy)-15-hydroxy-15,20-dimethyl-prostadien-16-inic Acid Methyl Ester At −70° under argon, 20.5 ml. of a lithium hexyne solution (prepared by adding, at −70°, dropwise 4.5 ml. of an approximately 2-molar butyllithium solution in hexane to a solution of 738 mg. of 1-hexyne in 16 ml. of absolute tetrahydrofuran and stirring for 10 minutes at −70°) was added dropwise to a solution of 1.50 g. of the ketone prepared according to Example 1(g) in 40 ml. of absolute ether and 40 ml. of absolute tetrahydrofuran. After 30 minutes at −70°, the mixture was introduced into 50 ml. of saturated ammonium chloride solution and extracted three times with 100 ml. of ether each time; the combined extracts were shaken with 40 ml. of saturated NaCl solution, dried over magnesium sulfate, and evaporated under vacuum. After column chromatography on silica gel (deactivated with 3% water) with ether/hexane (7+3), 1.28 g. of the title compound was obtained as a colorless oil (mixture of epimers).

TLC (ether): Rf value 0.60

IR: 3600, 3030, 2990, 2955, 2238, 1718, 1601, 1260, 980 cm$^{-1}$.

EXAMPLE 5

Methyl Ester of (5Z,13E)-(8R,9S,11R,12R,15S)-9,11,15-Trihydroxy-20-ethyl-15-methyl-prostadien-16-inic Acid and Methyl Ester of (5Z,13E)-(8R,9S,11R,12R,15R)-9,11,15-Trihydroxy-20-ethyl-15-methyl-prostadien-16-inic Acid A solution of 3.0 g. of (5Z,13E)-(8R,9S,11R,12R,15RS)-9,11-bis(benzoyloxy)-15-hydroxy-20-ethyl-15-methyl-prostadien-16-inic acid methyl ester in 140 ml. of absolute metanol was combined with 2.81 g. of anhydrous potassium carbonate. The mixture was agitated for 17 hours at room temperature under argon. After dilution with 750 ml. of ether, the mixture was shaken three times with respectively 80 ml. of water, dried over magnesium sulfate, and evaporated under vacuum. After chromatographing the residue on silica gel (deactivated with 3% water) with ether, 710 mg. of the 15S(15β)-configured title compound was obtained as a colorless oil and as the more polar component 720 mg. of the 15R(15β)-configured title compound as a colorless oil.

TLC (ether):
 (15S) Rf value 0.25
 (15R) Rf value 0.20

IR (15S): 3600, 3450 (wide), 2995, 2960, 2942, 2240, 1730, 970 cm$^{-1}$.

The IR spectrum of the 15R-configured compound is congruent.

The starting material for the above compounds was prepared as follows:

5(a)

(5Z,13E)-(8R,9S,11R,12R,15RS)-9,11-Bis(benzoyloxy)-20-ethyl-15-methyl-prostadien-16-inic Acid Methyl Ester At −70° under argon, 20 ml. of a lithium heptyne solution (prepared by adding dropwise at −70° 3 ml. of an approximately 2-molar butyllithium solution is hexane to a solution of 576 mg. of 1-heptyne in 17 ml. of tetrahydrofuran and stirring for 10 minutes at −70°) was added dropwie to a solution of 1.04 g. of the ketone produced according to Example 1 (g) in 50 ml. of absolute ether and 50 ml. of absolute tetrahydrofuran. After 30 minutes at −70°, the mixture was poured on 50 ml. of saturated ammonium chloride solution and extracted three times with respectively 80 ml. of ether. The combined ether extracts were shaken with 30 ml. of saturated NaCl solution, dried over magnesium sulfate, and evaporated to dryness under vacuum. After column chromatography on silica gel (deactivated with 3% water) with ether/hexane (7+3), 810 mg. of the title compound was obtained as a colorless oil (mixture of epimers).

TLC (ether): RF value 0.62

IR: 3600, 3030, 2995, 2955, 2240, 1718, 1600, 1260, 980 cm$^{-1}$.

EXAMPLE 6

Methyl Ester of (5Z,13E)-(8R,9S,11R,12R,15S)-9,11,15-Trihydroxy-15-methyl-17-(2-furyl)-18,19,20-trinor-prostadien-16-inic Acid and Methyl Ester of (5Z,13E)-(8R,9S,11R,12R,15R)-9,11,15-Trihydroxy-15-methyl-17-(2-furyl)-18,19,20-trinor-prostadien-16-inic Acid.

The procedure of Example 1 was followed, thus obtaining, from 1.47 g. of the methyl ester of (5Z,13E)-(8R,9S,11R,12R,15RS)-9,11-bis(benzoyloxy)-15-hydroxy-15-methyl-17-(2-furyl)-18,19,20-trinor-prostadien-16-inic acid, after carrying out a separation step, 305 mg. of the title compound having a 15S(15β)-configuration and 310 mg. of the title compound having a 15R(15β)-configuration, both in the form of colorless oils.

TLC (ether/dioxane):
(15S) Rf value 0.31
(15R) Rf value 0.25

IR (15S): 3600, 3400 (wide), 2998, 2955, 2240, 1725, 978 cm$^{-1}$.

IR (15R): 3600, 3400 (wide), 2998, 2955, 2240, 1725, 978 cm$^{-1}$.

6(a) The starting material for the above compounds was obtained from the methyl ester of (5Z, 13E)-(8R,9S,11R,12R)-9,11-bis(benzoyloxy)-15-oxo-17,18,19,20-tetranor-prostadienoic acid [see Example 1(g) with lithium-(2-furyl)-acetylide in 78% yield. In this step, the methyl ester of (5Z,13E)-(8R,9S,11R,12R,15RS)-9,11-bis(benzoyloxy)-15-hydroxy-15-methyl-17-(2-furyl)-18,19,20-trinor-prostadien-16-inic acid was produced as a colorless oil.

TLC (ether): Rf value 0.55

IR (in chloroform): 3600, 2998, 2955, 2945, 2238, 1716, 1620, 970 cm$^{-1}$.

EXAMPLE 7

Methyl Ester of (5Z,13E)-(8R,9S,11R,12R,15S)-9,11,15-Trihydroxy-15-methyl-17-(2-thienyl)-18,19,20-trinor-prostadien-16-inic Acid and Methyl Ester of (5Z,13E)-(8R,9S,11R,12R,15R)-9,11,15-Trihydroxy-15-methyl-17-(2-thienyl)-18,19,20-trinor-prostadien-16-inic Acid A solution of 2.0 g. of (5Z,13E)-(8R,9S,11R,12R,15RS)-9,11-bis(benzoyloxy)-15-hydroxy-15-methyl-17-(2-thienyl)18,19,20-trinor-prostadien-16-inic acid methyl ester in 80 ml. of absolute methanol was combined with 1.80 g. of anhydrous potassium carbonate and agitated for 15 hours at room temperature under argon. The mixture was then combined with 300 ml. of ether, shaken with 50 ml. of saturated NaCl solution, and drived over magnesium sulfate. The residue from the evaporation was separated by layer chromatography on silica gel plates with ether into the two desired epimers, thus obtaining 485 mg. of the 15S(15β) title compound and 470 mg. of the 15R(15α) title compound as color oils.

TLC (ether):
(15S) Rf value 0.19
(15R) Rf value 0.12

IR (15S): 3600, 3450 (wide), 2998, 2935, 2240, 1725, 978 cm$^{-1}$.

IR (15R): 3600, 3450 (wide), 2998, 2935, 2240, 1725, 978 cm$^{-1}$.

7(a) The starting material for the above compounds was obtained from (5Z,13E)-(8R, 9S,11R,12R)-9,11-bis(benzoyloxy)-15-oxo-17,18,19,20-tetranor-prostadienoic acid methyl ester [see Example 1(g)] with lithium-(2-thienyl)-acetylide in a 71% yield, analogously to Example 1(h). In this process, the methyl ester of (5Z,13E)-(8R,9S,11R,12R,15RS)-9,11-bis(benzoyloxy)-15-hydroxy-15-methyl-17-(2-thienyl)-18,19,20-trinor-prostadien-16-inic acid was obtained as a colorless oil.

TLC (ether): Rf value 0.53

IR (in chloroform): 3600, 2998, 2955, 2946, 2240, 1725, 970 cm$^{-1}$.

EXAMPLE 8

In accordance with Example 1(h), using the following organolithium compounds:
lithium-(2-pyridyl)-acetylide
lithium ethoxyacetylide
lithium phenoxyacetylide
lithium cyclohexylacetylide
lithium tert.-butylacetylide
by reaction with the methyl ester of (5Z,13E)-(8R,9S,11R,12R)-9,11-bis(benzoyloxy)-15-oxo-17,18,19,20-tetranor-prostadienoic acid [Example 1(g)] and subsequent reesterification according to Example 1, the compounds set forth hereinbelow are obtained:

(5Z,13E)-(8R,9S,11R,12R,15S)-9,11,15-trihydroxy-15-methyl-17-(2-pyridyl)-18,19,20-trinor-prostadien-16-inic acid methyl ester (5Z,13E)-(8R,9S,11R,12R,15R)-9,11,15-trihydroxy-15-methyl-17-(2-pyridyl)-18,19,20-trinor-prostadien-16-inic acid methyl ester (5Z,13E)-(8R,9S,11R,12R,15S)-9,11,15-trihydroxy-15-methyl-17-ethoxy-18,19,20-trinor-prostadien-16-inic acid methyl ester (5Z,13E)-(8R,9S,11R,12R,15R)-9,11,15-trihydroxy-15-methyl-17-ethoxy-18,19,20-trinor-prostadien-16-inic acid methyl ester (5Z,13E)-(8R,9S,11R,12R,15S)-9,11,15-trihydroxy-15-methyl-17-phenoxy-18,19,20-trinor-prostadien-16-inic acid methyl ester (5Z,13E)-(8R,9S,11R,12R,15R)-9,11,15-trihydroxy-15-methyl-17-phenoxy-18,19,20-trinor-prostadien-16-inic acid methyl ester (5Z,13E)-(8R,9S,11R,12R,15S)-9,11,15-trihydroxy-15-methyl-17-cyclohexyl-18,19,20-trinor-prostadien-16-inic acid methyl ester (5Z,13E)-(8R,9S,11R,12R,15R)-9,11,15-trihydroxy-15-methyl-17-cyclohexyl-18,19,20-trinor-prostadien-16-inic acid methyl ester (5Z,13E)-(8R,9S,11R,12R,15S)-9,11,15-trihydroxy-18,18-dimethyl-15-methyl-20-nor-prostadien-16-inic acid methyl ester (5Z,13E)-(8R,9S,11R,12R,15R)-9,11,15-trihydroxy-18,18-dimethyl-15-methyl-20-nor-prostadien-16-inic acid methyl ester.

EXAMPLE 9

Methyl Ester of (5Z,13E)-(8R,9S,11R,12R,15S)-9,11,15-Trihydroxy-20-ethyl-prostadien-16-inic Acid and Methyl Ester of (5Z,13E)-((8R,9S,11R,12R,15R)-9,11,15-Trihydroxy-20-ethyl-prostadien-16-inic Acid A solution of 1.80 g. of the methyl ester of (5Z,13E)-(8R,9S,11R,12R,15RS)-9,11-diacetoxy-20-ethyl-15-hydroxy-prostadien-16-inic acid in 70 ml. of absolute methanol was combined with 1.10 g. of anhydrous potassium carbonate. The mixture was agitated under argon for 15 hours at room temperature, then diluted with 250 ml. of ether, shaken three times with respectively 50 ml. of saturated NaCl solution, dried over magnesium sulfate, and evaporated to dryness under vacuum. After chromatography on silica gel (deactivated with 3% water) with ether/ethyl acetate (95+5), 610 mg. of the 15S(15β-OH)-configured title compound was obtained, as well as 615 mg. of the 15R(15α-OH)-configured title compound, both in the form of colorless oils.

TLC (ether):
(15S) Rf value 0.18
(15R) Rf value 0.14
IR (15S): 3600, 3440, (wide), 2998, 2960, 2940, 2238, 1730, 1600, 975 cm$^{-1}$.
IR (15R): 3600, 3440 (wide), 2998, 2960, 2940, 2938, 1730, 1600, 975 cm$^{-1}$.

The starting material for the above compounds was produced as follows:

9(a)

(5Z,13E)-(8R,9S,11R,12R,15RS)-9,11-Diacetoxy-20-ethyl-15-hydroxy-prostadien-16-inic Acid Methyl Ester At −70° under argon, 84 ml. of a lithium heptyne solution (prepared by adding dropwise at −70° 20 ml. of a 2-m butyl-lithium solution in hexane to a solution of 3.84 g. of 1-heptyne in 60 ml. of absolute tetrahydrofuran and stirring for 10 minutes at −70°) was added dropwise to a solution of 3.70 g. of the aldehyde obtained according to Example 2(f) in 250 ml. of absolute tetrahydrofuran and 200 ml. of absolute ether. The mixture was agitated for 60 minutes at −70°, then combined with 200 ml. of saturated ammonium chloride solution, allowed to warm up to room temperature, and extracted three times with respectively 200 ml. of ether. The organic phase was shaken twice with 100 ml. portions of water, dried over magnesium sulfate, and evaporated under vacuum. Chromatography on silica gel (deactivated with 3% water) yielded, with ether/hexane (6+4), 2.70 g. of the title compound as a colorless oil (mixture of epimers).

TLC (ether): Rf value 0.55
IR (chloroform): 3600, 2998, 2955, 2238, 1730, 1260, 978 cm$^{-1}$.

EXAMPLE 10

Analogously to Example 2(g), with the use of the following organolithium compounds:
lithium hexyne
lithium-(2-furyl)-acetylide
lithium-(2-thienyl)-acetylide
lithium-(2-pyridyl)-acetylide
lithium ethoxyacetylide
lithium phenoxyacetylide
lithium cyclohexylacetylide
lithium tert.-butylacetylide
by rection with the methyl ester of (5Z,13E)-(8R,9S,11R,12R)-9,11-bis)acetoxy)-15-oxo-16,17,18,19,20-pentanor-prostadienoic acid [from Example 2(f)]and subsequent reesterification according to Example 2, the compounds set forth hereinbelow are produced:

(5Z,13E)-(8R,9S,11R,12R,15S)-9,11,15-trihydroxy-20-methyl-prostadien-16-inic acid methyl ester
(5Z,13E)-(8R,9S,11R,12R,15R)-9,11,15-trihydroxy-20-methyl-prostadien-16-inic acid methyl ester
(5Z,13E)-(8R,9S,11R,12R,15R)-9,11,15-trihydroxy-17-(2-furyl)-18,19,20-trinor-prostadien-16-inic acid methyl ester
(5Z,13E)-(8R,9S,11R,12R,15R)-9,11,15-trihydroxy-17-(2-furyl)-18,19,20-trinor-prostadien-16-inic acid methyl ester
(5Z,13E)-(8R,9S,11R,12R,15S)-9,11,15-trihydroxy-17-(2-theinyl)-18,19,20-trinor-prostadien-16-inic acid methyl ester
(5Z,13E)-(8R,9S,11R,12R,15R)-9,11,15-trihydroxy-17-(2-thienyl)-18,19,20-trinor-prostadien-16-inic acid methyl ester
(5Z,13E)-(8R,9S,11R,12R,15S)-9,11,15-trihydroxy-17-(2-pyridyl)-18,19,20-trinor-prostadien-16-inic acid methyl ester
(5Z,13E)-(8R,9S,11R,12R,15R)-9,11,15-trihydroxy-17-(2-pyridyl)-18,19,20-trinor-prostadien-16-inic acid methyl ester
(5Z,13E)-(8R,9S,11R,12R,15S)-9,11,15-trihydroxy-17-ethoxy-18,19,20-trinor-prostadien-16-inic acid methyl ester
(5Z,13E)-(8R,9S,11R,12R,15R)-9,11,15-trihydroxy-17-ethoxy-18,19,20-trinor-prostadien-16-inic acid methyl ester
(5Z,13E)-(8R,9S,11R,12R,15S)-9,11,15-trihydroxy-17-phenoxy-18,19,20-trinor-prostadien-16-inic acid methyl ester
(5Z,13E)-(8R,9S,11R,12R,15R)-9,11,15-trihydroxy-17-phenoxy-18,19,20-trinor-prostadien-16-inic acid methyl ester
(5Z,13E)-(8R,9S,11R,12R,15S)-9,11,15-trihydroxy-17-cyclohexyl-18,19,20-trinor-prostadien-16-inic acid methyl ester
(5Z,13E)-(8R,9S,11R,12R,15R)-9,11,15-trihydroxy-17-cyclohexyl-18,19,20-trinor-prostadien-16-inic acid methyl ester
(5Z,13E)-(8R,9S,11R,12R,15S)-9,11,15-trihydroxy-18,18-dimethyl-20-nor-prostadien-16-inic acid methyl ester
(5Z,13E)-(8R,9S,11R,12R,15R)-9,11,15-trihydroxy-18,18-dimethyl-20-nor-prostadien-16-inic acid methyl ester.

EXAMPLE 11

Methyl Ester of (5Z)-(8R,9S,11R,12R,15S)-9,11,15-Trihydroxyprosten-16-inic Acid and Methyl Ester of (5Z)-(8R, 9S,11R,12R,15R)-9,11,15-Trihydroxyprosten-16-inic Acid From 2.0 g. of the methyl ester of (5Z)-(8R,9S,11R,12R,15RS)-9,11-bis(benzoyloxy)-15-hydroxy-prosten-16-inic acid (15-epimer mixture), 1.65 g. of crude product (mixture of the title compounds) was obtained with potassium carbonate in methanol analogously to Example 1. This product was separated by layer chromatography on silica gel plates with ether into the two epimeric alcohols, thus obtaining 234 mg. of the 15S(15β)-configured title compound and, as the more polar component, 211 mg. of the 15R(15α)-configured title compound, both in the form of oils.

TLC (ether/dioxane 9+1):
(15S) Rf value 0.29
(15R) Rf value 0.27
IR (15S): 3598, 3400 (wide), 2998, 2935, 2240, 1725 cm$^{-1}$
IR (15R): 3600, 3400 (wide), 2998, 2935, 2240, 1725 cm$^{-1}$ The starting material for the above title compounds was produced as follows:

11(a)
(1S,5R,6R,7R)-6-(Propan-3-al-1-yl)-7-benzoyloxy-2-oxabicyclo[3,3,0]octan-3-one A solution of 4.5 g. of the α,β-unsaturated aldehyde produced according to Example 3(a) in 200 ml. of ethyl acetate was reacted analogously to Example 13(a) with 180 mg. of palladium, 10% strength on charcoal. By chromatographing the residue on silica gel, 3.6 g. of the title compound was obtained with ether/hexane (8+2) as a yellowish oil.

TLC (ether): Rf value 0.40
IR (in chloroform):2950, 2740, 1765, 1725 cm$^{-1}$.

11(b)
(1S,5R,6R,7R)-6-[3,3-(2,2-Dimethyltrimethylenedioxy)-1-propyl]-7-benzoyloxy-2-oxabicyclo[3,3,0]octan-3-one 3.0 g. of the aldehyde produced according to Example 11(a), 1.8 g. of 2,2-dimethyl-propane-1,3-diol, and 30 mg. of p-toluenesulfonic acid in 120 ml. of benzene were heated for 1.5 hours underreflux with the use of a water trap. The mixture was worked up analogously to Example 1(c). Filtration over silica gel with ether/hexane (8+2) yielded 2.7 g. of the title compound as a waxy mass.

TLC (ether): Rf value 0.40
IR (in chloroform): 2950, 1770, 1720, 1600 cm$^{-1}$.

11(c) (2RS, 3aR,4R,5R,6aS)-4-[3,3-(2,2-Dimethyltrimethylenedioxy)-1-propyl]-2,5-dihydroxyperhydrocyclopenta[b]furan 2.5 g. of the compound produced according to Example 11(b) in 100 ml. of toluene was reacted with 24 ml. of a 20% solution of diisobutyl aluminum hydride in toluene, as set forth in Example 1(d), thus obtaining 1.8 g. of the title compound as a colorless oil.

IR (in chloroform): 3600, 3450 (wide), 2955 cm$^{-1}$.

11(d)
(5Z)-(8R,9S,11R,12R)-9,11-Dihydroxy-15,15-[(2,2-dimethyl)-trimethylenedioxy]-16,17,18,19,20-pentanor-prostenoic Acid Methyl Ester A solution of 6.7 g. of 4-lcarboxybutyltriphenylphosphonium bromide in 25 ml. of dimethyl sulfoxide was combined dropwise with 26.5 ml. of a solution of methanesulfinylmethylsodium in DMSO (prepared by dissolving 1.4 g. of 50% sodium hydride suspension in 26.5 ml. of DMSO during the course of one hour at 70°-75°), and the mixture was stirred for 30 minutes at room temperature. This red ylene solution was added dropwise to a solution of 0.75 of the lactol obtained according to Example 11(c) in 12.5 ml. of DMSO, and the mixture as agitated for 2 hours at 50°. Thereafter, the DMSO was extensively distilled off under vacuum; the mixture was combined with 50 ml. of ice water and extracted three times with ether. This ether extract was discarded. The aqeuous phase was acidified to pH 5 with 10% citric acid solution and extracted four times with a mixture of hexane/ether (1+2). The organic phase was shaken with brine, dried over magnesium sulfate, and evaporated under vacuum. In this way, 1.6 g. of a crude product was obtained which was esterified without any further purification in 50 ml. of methylene chloride with 10 ml. of an ethereal diazomethane solution (see "Organikum" p. 528). After chromatographing the residue from the evaporation on silica gel, 0.65 g. of the title compound was obtained with ether as a colorless oil.

TLC (ether/dioxane 9+1): Rf value 0.48
IR (in chloroform): 3600, 2950, 1730, 970 cm$^{-1}$.

11(e)
(5Z)-(8R,9S,11R,12R)-9,11-Dihydroxy-15-oxo-16,17,18,19,20-pentanor-prostenoic Acid Methyl Ester 3.0 g. of the compound prepared according to Example 11(d) was agitated for 4 hours at 50° in 50 ml. of a mixture of glacial acetic acid/water/tetrahydrofuran (65/35/10) analogously to Example 1(f), thus obtaining with ether/ethyl acetate (8+2) 2.3 g. of the title compound as a colorless oil.

TLC (ether/dioxane 9+1): Rf value 0.28
IR (in chloroform): 3600, 3450, 2955, 2740, 1720 (wide) cm$^{-1}$.

11(f)
(5Z)-(8R,9S,11R,12R)-9,11-Bis(benzoyloxy)-15-oxo-16,17,18,19,20-pentanor-prostenoic Acid Methyl Ester A solution of 2.2 g. of the aldehyde prepared according to Example 11(e) in 10 ml. of pyridine was reacted analogously to Example 1(g) with 4 ml. of benzoyl chloride. With ether/hexane (8+2), 2.1 g. of the title compound was obtained as a colorless oil.

TLC (ether/hexane 7+3): Rf value 0.15
IR (in chloroform): 3030, 3000, 2955, 2740, 1715 (wide) 1600, 1583, 1589, 1450, 1265, 1020 cm$^{-1}$.

11(g)
(5Z)-(8R,9S,11R,12R,15RS)-9,11-Bis(benzoyloxy)-15-hydroxy-prostadien-16-inic Acid Methyl Ester At −70° under argon, 60 ml. of a lithium pentyne solution was added dropwise to a solution of 2.70 g. of the compound produced according to Example 11(f) in205 ml. of tetrahydrofuran (absolute) and 145 ml. of ether (absolute). The mixture was agitated for 30 minutes at −70°, then combined with 100 ml. of saturated ammonium chloride solution. The mixture was allowed to warm up to room temperature, extracted three times with ether, the organic phase was shaken with water, dried with sodium sulfate, and evaporated under vacuum. After chromatography on silica gel (deactivated with 3% water), the yield was, with ether/hexane (7+3), 2.1 g. of the title compound as a colorless oil (mixture of epimers).

TLC (ether): Rf value 0.50
IR (in chloroform): 3600, 3030, 3000, 2950, 2945, 2240 (weak), 1715, 1602, 1270 cm$^{-1}$.

EXAMPLE 12

Methyl Ester of
(13E)-(8R,9S,11R,12R,15R)-9,11,15-Trihydroxyprosten-16-inic Acid and Methyl Ester of
(13E)-(8R,9S,11R,12R,15S)-9,11,15-Trihydroxyprosten-16-inic Acid From 400 mg. of the methyl ester of (13E)-(8R,9S,11R,12R,15RS)-9,11-bis(acetoxy)15-hydroxy-prosten-16-inic acid in 20 ml. of absolute methanol, there were obtained with 280 mg. of anhydrous potassium carbonate analogously to Example 1 118 mg. of the 15R-configured (15α-hydroxy) title compound and, as the less polar component, 111 mg. of the 15S-configured (15β-hydroxy) title compound as colorless oils.

TLC (ether):
  15R: Rf value 0.11
  15S: Rf value 0.14
IR (in chloroform):
  (15R): 3600, 3450, 3000, 2937, 2235, 1725, 1600 cm$^{-1}$.

The 15S title compound showed an almost identical IR spectrum.

The starting material for the above title compounds was produced as set forth below:

12(a)
(8R,9S,11R,12R)-9,11-Bis(acetoxy)-13,13-diethoxy-14,15,16,17,18,19,20-heptanorprostanoic Acid Methyl Ester A solution of 4.0 g. of the compound prepared according to Example 2(d) in 180 ml. of ethyl acetate was shaken, with the addition of 160 mg. of palladium, 10% strength, on charcoal, for two hours at room temperature under a hydrogen atmosphere. Subsequently, the mixture was filtered and evaporated under vacuum, thus obtaining 3.98 g. of the title compound as a colorless oil.

TLC (ether): Rf value 0.88

The NMR spectrum did not show any olefinic protons.

12(b)
(8R,9S,11R,12R)-9,11-Bis(acetoxy)-12-formyl-13,14,15,16,17,18,19,20-octanor-prostanoic Acid Methyl Ester 2.0 g. of the compound prepared according to Example 12(a) was agitated for 16 hours at room temperature in 40 ml. of a mixture of glacial acetic acid/water/tetrahydrofuran (65/35/10) and evaporated to dryness under vacuum. In this way, 1.7 g. of the title compound, uniform as determined by thin-layer chromatography, was obtained as a light-yellow oil.

TLC (ether): Rf value 0.72
IR: 2958, 2730, 1730 (wide), 1245 cm$^{-1}$.

12(c)
(13E)-(8R,9S,11R,12R)-9,11-Bis(acetoxy)-15-oxo-16,17,18,19,20-pentanor-prostenoic Acid Methyl Ester A mixture of 2.0 g. of the aldehyde obtained according to Example 12(b), 1.72 g. of formylmethylenetriphenylphosphorane (J. Chem. Soc. 1961, 2130), 20 mg. of benzoic acid, and 45 ml. of benzene was agitated for 48 hours at room temperature under argon. After chromatographing the residue from the evaporation on silica gel with ether/hexane (8+2), the yield was 972 mg. of the title compound as a colorless oil.

TLC (ether): Rf value 0.43
IR: 2955, 2855, 2740, 1730, 1687, 1640, 1435, 1375, 1240, 970 cm$^{-1}$.

12(d)
(13E)-(8R,9S,11R,12R,15RS)-9,11-Bis(acetoxy)-15-hydroxy-prosten-16-inic acid Methyl Ester At −70° and under argon, 30 ml. of a lithium pentyne solution was added dropwise to a solution of 0.95 g. of the compound obtained according to Example 12(c) in 75 ml. of tetrahydrofuran (absolute) and 50 ml. of ether (absolute). The mixture was stirred for 60 minutes at −70°, combined with 60 ml. of saturated ammonium chloride solution, allowed to warm up to room temperature, and extracted three times with respectively 100 ml. of ether. The organic phase was shaken twice with 30 ml. portions of water, dried over sodium sulfate, and evaporated under vacuum. After chromatography on silica gel (deactivated with 3% water), 0.65 g. of the title compound was obtained with hexane/ether (6+4) as a colorless oil.

TLC (ether): Rf value 0.47
IR (in chloroform): 3600, 3030, 2998, 2955, 2240, 1730, 978 cm$^{-1}$.

EXAMPLE 13

Methyl Ester of
(5Z)-(8R,9S,11R,12R,15S)-9,11,15-Trihydroxy-15-methyl-prosten-16-inic Acid and Methyl Ester of
(5Z)-(8R,9S,11R,12R,15R)-9,11,15-Trihydroxy-15-methyl-prosten-16-inic Acid From a solution of 1.20 g. of the methyl ester of (5Z)-(8R,9S,11R,12R,15RS)-9,11-bis(benzoyloxy)-15-hydroxy-15-methyl-prostadien-16-inic acid in 50 ml. of absolute methanol, there were obtained with 1.18 g. of anhydrous potassium carbonate analogously to Example 1, after column chromatography with ether/ethyl acetate (9+1), 171 mg. of the 15S(15β)-configured title compound as a colorless oil and, as the more polar component, 153 mg. of the 15R(15α)-configured title compound as a colorless oil.

TLC (ether):
  (15S) Rf value 0.20
  (15R) Rf value 0.18
IR (15S): 3600, 3450, 2995, 2960, 2240, 1730 cm$^{-1}$.
The IR of the 15R-compound was identical.

The starting material for the above compounds was prepared as follows:

13(a)
(1S,5R,6R,7R)-6-(3-Oxo-1-butyl)-7-benzoyloxy-2-oxabicyclo[3,3,0]octan-3-one A solution of 5 g. of the α,β-unsaturated ketone prepared according to Example 1 (b) in 200 ml. of ethyl acetate was shaken, with the addition of 200 mg. of palladium, 10% on charcoal, for two hours at room temperature under a hydrogen atmosphere. After filtration and evaporation of the solution, 5 g. of the title compound was obtained as a colorless oil which was completely uniform as determined by thin-layer chromatography.

TLC (ether): Rf value 0.41
IR: 2950, 1770, 1720 (wide), 1600 cm$^{-1}$.

13(b)
(1S,5R,6R,7R)-6-[3,3-(2,2-Dimethyltrimethylenedioxy)-1-butyl]-7-benzoyloxy-2oxabicyclo-[3,3,0]octan-3-one 1.50 g. of the ketone prepared according to Example 13(a), 0.9 g. of 2,2-dimethyl-propane-1,3-diol, 15 mg. of p-toluenesulfonic acid in 60 ml. of benzene were reacted analogously to Example 1(c). The yield was 1,35 g of the title compound as a colorless oil.

IR: 2950, 1765, 1715, 1600 cm$^1$.

13(c)
(2RS,3aR,4R,5R,6aS)-4-[3,3-(2,2-Dimethyltrimethylenedioxy)-1-butyl]-2,5-dihydroxyperhydrocyclopenta[b]furan 4.50 g. of the compound produced according to Example 13(b) in 250 ml. of toluene was reacted analogously to Example 1(d) with 45 ml. of a 20% solution of diisobutyl aluminum hydride in toluene, thus obtaining 3.1 g. of the title compound as a colorless oil.

IR: 3600, 3450 (wide), 2955 cm$^{-1}$.

13(d)
(5Z)-(8R,9S,11R,12R)-9,11-Dihydroxy-15,15-[(2,2-dimethyl)-trimethylenedioxy]-17,18,19,20-tetranor-prostenoic Acid Methyl Ester 53 ml. of a solution of methanesulfinylmethylsodium in DMSO (prepared by dissolving 2.65 g. of 50% sodium hydride suspension in 53 ml. of DMSO during the course of one hour at 70°–75°) was added dropwise to a solution of 13.4 g. of 4-carboxybutyltriphenylphosphonium bromide in 50 ml. of dimethyl sulfoxide. The mixture was stirred for 30 minutes at room temperature. This red ylene solution was then added dropwise to a solution of 1.50 g. of the lactol obtained according to Example 13(c) in 25 ml. of DMSO, and the mixture was stirred for 2 hours at 50°. Subsequently, the DMSO was distilled off extensively under vacuum, combined with 100 ml. of ice water, and extracted three times with ether. This ether extract was discarded. The aqueous phase was acidified to pH 5 with 10% citric acid solution and extracted four times with a mixture of hexane/ether (1+2). The organic phase was shaken with brine, dried over magnesium sulfate, and evaporated under vacuum. In this way, 3.2 g. of a crude product was formed which was esterified without any further purification in 50 ml. of methylene chloride with 20 ml. of an ethereal diazomethane solution (see "Organikum" p. 528). After chromatography of the evaporation residue on silica gel, 1.71 g. of the title compound was obtained with ether as a colorless oil.

TLC (ether/dioxane 9+1): Rf value 0.50
IR (in chloroform): 3600, 2950, 1730 cm$^{-1}$.

13(e)
(5Z)-(8R,9S,11R,12R)-9,11-Dihydroxy-15-oxo-17,18,19,20-tetranor-prostenoic Acid Methyl Ester 6.7 g. of the compound prepared according to Example 13(d) was reacted analogously to Example 1(f), thus obtaining 4.6 g. of the title compound as a colorless oil.

TLC (ether/dioxane 9+1): Rf value 0.30
IR (in chloroform): 3600, 3450, 2955, 1725, 1692, 1670, 1623 cm$^{-1}$.

13(f)
(5Z)-(8R,9S,11R,12R)-9,11-Bis(benzoyloxy)-15-oxo-17,18,19,20-tetranor-prostenoic Acid Methyl Ester A solution of 4.60 g. of the ketone prepared according to Example 13(e) in 20 ml. of pyridine was reacted analogously to Example 1(g), thus producing 4.06 g. of the title compound as a colorless oil.

TLC (ether/hexane 7+3): Rf value 0.18
IR (in chloroform): 3030, 3000, 2955, 1715, 1672, 1625, 1600, 1583, 1589, 1450, 1265, 1024 cm$^{-1}$.

13(g)
(5Z)-(8R,9S,11R,12R,15RS)-9,11-Bis(benzoyloxy)-15-hydroxy-15-methyl-prosten-16-inic Acid Methyl Ester At −70° under argon, 13 ml. of a lithium pentyne solution (prepared by adding dropwise to a solution of 394 mg. of 1-pentyne in 10.5 ml. of absolute tetrahydrofuran at 70° 2.5 ml of an approximately 2-molar butyllithium solution in hexane and stirring the mixture for 10 minutes at −70°) was added dropwise to a solution of 0.84 g. of the ketone produced according to Example 13(f) in 25 ml. of absolute ether and 20 ml. of absolute tetrahydrofuran. The mixture was agitated for 30 minutes at −70°, combined with 30 ml. of saturated ammonium chloride solution, and extracted three times with respectively 100 ml. of ether. The combined ether extracts were shaken with 50 ml. of saturated NaCl solution, dried over magnesium sulfate, and evaporated to dryness under vacuum. Column chromatography on silica gel (deactivated with 3% water) with ether/hexane (7+3) yielded 0.7 g. of the title compound (mixture of epimers) as a colorless oil.

TLC (ether): Rf value 0.57
IR: 3600, 3030, 2955, 2240, 1717, 1600, 1265 cm$^1$.

EXAMPLE 14
Methyl Ester of (13E)-(8R,9S,11R,12R,15S)-9,11,15-Trihydroxy-15-methyl-prosten-16-inic Acid and Methyl Ester of (13E)-(8R,9S,11R,12R,15R)-9,11,15-Trihydroxy-15-methyl-prosten-16-inic Acid A solution of 1.38 g. of (13E)-(8R,9S,11R,12R,15RS)-9,11-bis(benzoyloxy)-15-hydroxy-15-methyl-prosten-16-inic acid methyl ester in 50 ml. of absolute methanol was combined with 1.25 g. of anhydrous potassium carbonate and agitated for 15 hours at room temperature under argon. After dilution with 300 ml. of ether, the mixture was shaken three times with respectively 50 ml. of water, dried over magnesium sulfate, and evaporated under vacuum. After chromatography of the residue on silica gel (deactivated with 3% water), there were obtained, with ether/ethyl acetate (9+1), 250 mg. of the 15S(15β)-configured title compound as a colorless oil and, as the more polar component, 275 mg. of the 15R(15α)-configured title compound as a colorless oil.

TLC (ether):
(15S) Rf value 0.20
(15R) Rf value 0.14

IR (15S and 15R compounds were almost identical): 3600, 3450, 2995, 2960, 2940, 2240, 1728, 1600, 975 cm$^{-1}$ The starting material for the above compounds was prepared as follows:

14(a)

(13E)-(8R,9S,11R,12R)-9,11-Bis(benzoyloxy)-15-oxo-17,18,19,20-tetranor-prostenoic Acid Methyl Ester A mixture of 520 mg. of the methyl ester of (5Z,13E)-(8R,9S,11R,12R)-9,11-bis(benzoyloxy)-15-oxo-17,18,19,20-tetranor-prostadienoic acid (prepared according to Example 1[g]), 50 mg. of 10% palladium on charcoal, and 60 ml. of ethyl acetate was agitated at −20° under a hydrogen atmosphere. The course of the hydrogenation reaction was followed by thin-layer chromatography. After the absorption of 23.1 ml. of hydrogen (after 2 hours), the reaction mixture was filtered through a glass suction filter and evaporated to dryness under vacuum, thus obtaining 510 mg. of the title compound as a colorless oil.

TLC (ether/hexane 7+3): Rf value 0.20
IR (in chloroform): 3030, 3000, 2950, 1715, 1672, 1625, 1600, 978 cm$^{-1}$.

14(b)

(13E)-(8R,9S,11R,12R,15RS)-9,11-Bis(benzoyloxy)-15-hydroxy-15-methyl-prosten-16-inic Acid Methyl Ester At −70° under argon, 26 ml. of a lithium pentyne solution (prepared by adding dropwise to a solution of 788 mg. of 1-pentyne in 21 ml. of absolute tetrahydrofuran at −70° 5 ml. of an approximately 2-molar butyllithium solution in hexane and stirring for 10 minutes at −70°) was added dropwise to a solution of 1.71 g. of the ketone prepared according to Example 14(a) in 50 ml of absolute ether and 40 ml. of absolute tetrahydrofuran. The mixture was agitated for 30 minutes at −70°, combined with 60 ml. of saturated ammonium chloride solution, and extracted three times with respectively 100 ml. of ether. The combined ether extracts were shaken with 50 ml. of saturated NaCl solution, dried over magnesium sulfate, and evaporated to dryness under vacuum. After column chromatography on silica gel (deactivated with 3% water) with ether/hexane (7+3), 1.25 g. of the title compound (mixture of epimers) was obtained as a colorless oil.

TLC (ether): Rf value 0.57
IR: 3600, 3030, 2995, 2955, 2240, 1717, 1600, 1265, 978 cm$^{-1}$.

EXAMPLE 15

Methyl Ester of (8R,9S,11R,12R,15S)-9,11,15-Trihydroxy-15-methyl-prostan-16-inic Acid and Methyl Ester of (8R,9S,11R,12R,15R)-9,11,15-Trihydroxy-15-methyl-prostan-16-inic Acid Analogously to Example 1, from a solution of 3.0 g. of (8R,9S,11R,12R,15RS)-9,11-bis (benzoyloxy)-15-hydroxy-15-methyl-prostan-16-inic acid methyl ester in 140 ml. of absolute methanol, with 2.75 g. of anhydrous potassium carbonate, the yield was 215 mg. of the 15S(15β)-configured title compound as a colorless oil and, as the more polar component, 315 mg. of the 15R(15α)-configured title compound as a colorless oil.

TLC (ether):
(15S) Rf value 0.26
(15R) Rf value 0.24
IR (15S): 3600, 3450 (wide), 2995, 2960, 2942, 2240, 1730 cm$^{-1}$.

The IR spectrum of the 15R-configured compound is congruent.

The starting material for the above title compounds was produced as set forth below:

15(a)

(8R,9S,11R,12R)-9,11-Bis(benzoyloxy)-15-oxo-17,18,19,20-tetranor-prostanoic Acid Methyl Ester A mixture of 1.4 g. of (5Z,13E)-(8R,9S,11R,12R)-9,11-bis(benzoyloxy)-15-oxo-17,18,19,20-tetranor-prostadienoic acid methyl ester (Example 1[g]), 100 mg. of 10% palladium on charcoal, and 120 ml. of ethyl acetate was agitated for 2 hours at room temperature under a hydrogen atmosphere. Thereafter, the mixture was filtered through a glass suction filter and evaporated under vacuum, thus obtaining 1.38 g. of the title compound as a colorless oil.

TLC (ether/hexane 7+3): Rf value 0.22
IR (in chloroform): 3030, 2998, 2945, 1715 (wide), 1600, 1265 cm$^{-1}$.

The NMR spectrum in CDCl$_3$ did not show any olefinic protons.

15(b)

(8R,9S,11R,12R,15RS)-9,11-Bis(benzoyloxy)-15-methyl-prostan-16-inic Acid Methyl Ester At −70° under argon, 26 ml. of a lithium pentyne solution (prepared by adding dropwise at −70° to a solution of 788 mg. of 1-pentyne in 21 ml. of absolute tetrahydrofuran 5 ml. of a 2-molar butyllithium solution in hexane and stirring for 10 minutes at −70°) was added dropwise to a solution of 1.68 g. of the ketone prepared according to Example 15(a) in 50 ml. of absolute ether and 40 ml. of tetrahydrofuran. The mixture was agitated for 30 minutes at −70°, combined with 60 ml. of saturated ammonium chloride solution, and extracted three times with respectively 100 ml. of ether. The combined ether extracts were shaken with 50 ml. of saturated NaCl solution, dried over magnesium sulfate, and evaporated. After column chromatography on silica gel (deactivated with 3% water), 1.4 g. of the title compound (mixture of epimers) was obtained with ether/hexane (7+3) in the form of a colorless oil.

TLC (ether): Rf value 0.59
IR: 3600, 3030, 2996, 2955, 2240, 1716, 1600 cm$^{-1}$.

EXAMPLE 16

(5Z,13E)-(8R,9S,11R,12R,15S)-9,11,15-Trihydroxy-15-methylprostadien-16-inic Acid 190 mg. of the methyl ester of (5Z,13E)-(8R,9S,11R,12R,15S)-9,11,15-trihydroxy-15-methyl-prostadien-16-inic acid (prepared according to Example 1) was agitated for 16 hours at room temperature under argon in a mixture of 80 mg. of potassium carbonate, 10 ml. of methanol, and 2 ml. of water. The mixture was concentrated under vacuum, combined with 30 ml. of saturated NaCl solution, adjusted to pH 6 with 5% citric acid solution, extracted three times with respectively 60 ml. of methylene chloride, and the organic phase was shaken twice with respectively 20 ml. of saturated NaCl solution. The mixture was then dried over sodium sulfate and evaporated under vacuum, thus producing 165 mg. of the title compound as a colorless oil which was completely uniform as determined by thin-layer chromatography.

TLC (chloroform/isopropanol 85+15): Rf value 0.35
IR: 3600-3300, 2998, 2960, 2938, 2240, 1715, 975 cm$^{-1}$.

EXAMPLE 17

(5Z,13E)-(8R,9S,11R,12R,15R)-9,11,15-Trihydroxy-15-methylprostadien-16-inic Acid From 200 mg. of the methyl ester (5Z,13E)-(8R,9S,11R,12R,15R)-9,11,15-trihydroxy-15-methyl-prostadien-16-inic acid (prepared according to Example 1), 168 mg. of the title compound was obtained analogously to Example 16 as a colorless oil.

TLC (chloroform/isopropanol 85+15): Rf value 0.32
IR: 3600-3300, 2997, 2960, 2938, 2238, 1715, 975 cm$^{-1}$.

EXAMPLE 18

(5Z,13E)-(8R,9S,11R,12R,15S)-9,11,15-Trihydroxy-20-20-ethyl-15-methyl-prostadien-16-inic Acid From 200 mg. of the 15S-configured compound prepared according to Example 5, 183 mg. of the title compound was obtained analogously to Example 16 in the form of a colorless oil.

TLC (chloroform/isopropanol 85+15): Rf value 0.36
IR: 3600-3300, 2998, 2960, 2940, 2240. 1715, 975 cm$^{-1}$.

EXAMPLE 19

(5Z,13E)-(8R,9S,11R,15R)-9,11,15-Trihydroxy-20-ethyl-15-methyl-prostadien-16-inic Acid Analogously to Example 16, 170 mg. of the title compound was obtained as a colorless oil from 190 mg. of the 15R-configured compund prepared according to Example 5.

TLC (chloroform/isopropanol 85+15): Rf value 0.34
IR: 3600-3300, 2998, 2960, 2940, 2240, 1715, 975 cm$^{-1}$.

EXAMPLE 20

In analogy to the saponification described in Example 16, the following prostaglandin acids are obtained:

(5Z,13E)-(8R,9S,11R,12R,15S)-9,11,15-trihydroxy-15,20-dimethylprostadien-16-inic acid
(5Z,13E)-(8R,9S,11R,12R,15R)-9,11,15-trihydroxy-15,20-dimethylprostadien-16-inic acid
(5Z,13E)-(8R,9S,11R,12R,15S)-9,11,15-trihydroxy-15-methyl-17-(2-furyl)-18,19,20-trinor-prostadien-16-inic acid
(5Z,13E)-(8R,9S,11R,12R,15R)-9,11,15-trihydroxy-15-methyl-17-(2-furyl)-18,19,20-trinor-prostadien-16-inic acid
(5Z,13E)-(8R,9S,11R,12R,15S)-9,11,15-trihydroxy-15-methyl-17-(2-thienyl)-18,19,20-trinor-prostadien-16-inic acid
(5Z,13E)-(8R,9S,11R,12R,15R)-9,11,15-trihydroxy-15-methyl-17-(2-thienyl)-18,19,20-trino-prostadien-16-inic acid
(5Z,13E)-(8R,9S,11R,12R,15S)-9,11,15-trihydroxy-15-methyl-17-(2-pyridyl)-18,19,20-trinor-prostadien-16-inic acid
(5Z,13E)-(8S,9S,11R,12R,15R)-9,11,15-trihydroxy-15-methyl-17-(2-pyridyl)-18,19,20-trinor-prostadien-16-inic acid
(5Z,13E)-(8R,9S,11R,12R,15S)-9,11,15-trihydroxy-15-methyl-17-ethoxy-18,19,20-trinor-prostadien-16-inic acid
(5Z,13E)-(8R,9S,11R,12R,15R)-9,11,15-trihydroxy-15-methyl-17-ethoxy-18,19,20-trinor-prostadien-16-inic acid
(5Z,13E)-(8R,9S,11R,12R,15S)-9,11,15-trihydroxy-15-methyl-17-phenoxy-18,19,20-trinor-prostadien-16-inic acid
(5Z,13E)-(8R,9S,11R,12R,15R)-9,11,15-trihydroxy-15-methyl-17-phenoxy-18,19,20-trinor-prostadien-16-inic acid
(5Z,13E)-(8R,9S,11R,12R,15S)-9,11,15-trihydroxy-15-methyl-17-cyclohexyl-18,19,20-trinor-prostadien-16-inic acid
(5Z,13E)-(8R,9S,11R,12R,15R)-9,11,15-trihydroxy-15-methyl-17-cyclohexyl-18,19,20-trinor-prostadien-16-inic acid
(5Z,13E)-(8R,9S,11R,12R,15S)-9,11,15-trihydroxy-18,18-dimethyl-15-methyl-20-nor-prostadien-16-inic acid
(5Z,13E)-(8R,9S,11R,12R,15R)-9,11,15-trihydroxy-18,18-dimethyl-15-methyl-20-nor-prostadien-16-inic acid
(5Z,13E)-(8R,9S,11R,12R,15S)-9,11,15-trihydroxy-prostadien-16-inic acid
(5Z,13E)-(8R,9S,11R,12R,15R)-9,11,15-trihydroxy-prostadien-16-inic acid
(5Z,13E)-(8R,9S,11R,12R,15S)-9,11,15-trihydroxy-20-ethylprostadien-16-inic acid
(5Z,13E)-(8R,9S,11R,12R,15R)-9,11,15-trihydroxy-20-ethylprostadien-16-inic acid
(5Z,13E)-(8R9S,11R,12R,15S)-9,11,15-trihydroxy-20-methylprostadien-16-inic acid
(5Z,13E)-(8R,9S,11R,12R,15-trihydroxy-20-methyl-prostadien-16-inic acid
(5Z,13E)-(8R,9S,11R,12R,15S)-9,11,15-trihydroxy-17-(2-furyl)-18,19,20-trinor-prostadien-16-inic acid
(5Z,13E)-(8R9S,11R,12R,15R)-9,11,15-trihydroxy-17-(2-furyl)-18,19,20-trinor-prostadien-16-inic acid
(5Z,13E)-(8R,9S,11R,12R,15S)-9,11,15-trihydroxy-17-(2-thienyl)-18,19,20-trinor-prostadien-16-inic acid
(5Z,13E)-(8R,9S,11R,12R,15R)-9,11,15-trihydroxy-17-(2-thienyl)-18,19,20-trinor-prostadien-16-inic acid
(5Z,13E)-(8R,9S,11R,12R,15S)-9,11,15-trihydroxy-17-(2-pyridyl)-18,19,20-trinor-prostadien-16-inic acid
(5Z,13E)-(8R,9S,11R,12R,15R)-9,11,15-trihydroxy-17-(2-pyridyl)-18,19,20-trinor-prostadien-16-inic acid
(5Z,13E)-(8R,9S,11R,12R,15S)-9,11,15-trihydroxy-17-ethoxy-18,19,20-trinor-prostadien-16-inic acid
(5Z,13E)-(8R,9S,11R,12R,15R)-9,11,15-trihydroxy-17-ethoxy-18,19,20-trinor-prostadien-16-inic acid
(5Z,13E)-(8R,9S,11R,12R,15S)-9,11,15-trihydroxy-17-phenoxy-18,19,20-trinor-prostadien-16-inic acid
(5Z,13E)-(8R,9S,11R,12R,15R)-9,11,15-trihydroxy-17-phenoxy-18,19,20-trinor-prostadien-16-inic acid
(5Z,13E)-(8R,9S,11R,12R,15S)-9,11,15-trihydroxy-17-cyclohexyl-18,19,20-trinor-prostadien-16-inic acid
(5Z,13E)-(8R,9S,11R,12R,15R)-9,11,15-trihydroxy-17-cyclohexyl-18,19,20-trinor-prostadien-16-inic acid
(5Z,13E)-(8R,9S,11R,12R,15S)-9,11,15-trihydroxy-18,18-dimethyl-20-nor-prostadien-16-inic acid
(5Z,13E)-(8R,9S,11R,12R,15R)-9,11,15-trihydroxy-18,18-dimethyl-20-nor-prostadien-16-inic acid
(5Z)-(8R,9S,11R,12R,15S)-9,11,15-trihydroxy-15-methyl-prosten-16-inic acid
(5Z)-(8R,9S,11R,12R,15R)-9,11,15-trihydroxy-15-methyl-prosten-16-inic acid
(13E)-(8R,9S,11R,12R,15S)-9,11,15-trihydroxy-15-methyl-prosten-16-inic acid (13E)-(8R,9S, 11R,12R,15R)-9,11,15-trihydroxy-15-methyl-prosten-16-inic acid
(8R,9S,11R12R,15S)-9,11,15-trihydroxy-15-methyl-prostan-16-inic Acid
(8R,9S,11R,12R,15R)-9,11,15-trihydroxy-15-methyl-prostan-16-inic acid
(5Z)-(8R,9S,11R,12R,15S)-9,11,15-trihydroxy-prosten-16-inic acid
(5Z)-(8R,9S,11R12R,15R)-9,11,15-trihydroxy-prosten-16-inic acid
(13E)-(8R,9S,11R,12R,15S)-9,11,15-trihydroxy-prosten-16-inic acid
(13E)-(8R,9S,11R,12R,15R)-9,11,15-trihydroxy-prosten-16-inic acid
(8R9S,11R,12R15S)-9,11,15-trihydroxy-prostan-16-inic acid
(8R,9S,11R,12R,15R)-9,11,15-trihydroxy-prostan-16-inic acid.

EXAMPLE 21

(5Z,13E)-(8R,11R,12R,15S)-11,15-Dihydroxy-15-methyl-9-oxoprostadien-16-inic Acid Under a hydrogen atmosphere, 2 g. of platinum oxide was shaken in 15 ml. of ethyl acetate for 2 hours at room temperature. After the hydrogen had been displaced by nitrogen, the mixture was shaken for 3 hours under an oxygen atmosphere and then combined with a solution of 225 mg. of the compound prepared according to Example 16 in 5 ml. of ethyl acetate. The mixture was then stirred for 48 hours at room temperature under an oxygen atmosphere, filtered, and evaporated under vacuum. After chromatography on silica gel (deactivated with 3% water), 105 mg. of the title compound was obtained with methylene chloride/ethyl acetate (9+1) in the form of a colorless oil.
TLC (chloroform/isopropanol 85+15): Rf value 0.46
IR: 3600-3300, 3000, 2960, 2940, 2240, 1740, 1710, 976 cm$^{-1}$.

EXAMPLE 22

(5Z,13E)-(8R,11R,12R,15R)-11,15-Dihydroxy-15-methyl-9-oxoprostadien-16-inic Acid In accordance with the process described in Example 21, 92 mg. of the title compound was obtained as a colorless oil from 175 mg. of the compound produced according to Example 17.
TLC (chloroform/isopropanol 85+15): Rf value 0.43.
IR: 3600-3300, 3000, 2960, 2940, 2240. 1740, 1710, 975 cm$^{-1}$.

EXAMPLE 23

In analogy to the oxidation described in Example 21, the 9-oxo-prostaglandins set forth below are obtained from the 15-methyl-substituted prostaglandin acids:
(5Z,13E)-(8R,11R,12R15S)-11,15-hydroxy-15-methyl-20-ethyl-9-oxo-prostadien-16-inic acid
(5Z,13E)-(8R,11R,12R,15R)-11,15-dihydroxy-15-methyl-20-ethyl-9-oxo-prostadien-16-inic acid
(5Z,13E)-(8R,11R,12R,15S)-11,15-dihydroxy-15,20-dimethyl-9-oxo-prostadien-16-inic acid
(5Z,13E)-(8R,11R,12R,15R)-11,15-dihydroxy-15,20-dimethyl-9-oxo-prostadien-16-inic acid
(5Z,13E)-(8R11R,12R,15S)-11,15-dihydroxy-15-methyl-9-oxo-17-(2-thienyl)-18,19,20-trinor-prostadien-16-inic acid
(5Z,13E)-(8R,11R,12R,15R)-11,15-dihydroxy-15-methyl-9-oxo-17-(2-thienyl)-18,19,20-trinor-prostadien-16-inic acid
(5Z,13E)-(8R,11R,12R,15S)-11,15-dihydroxy-15-methyl-9-oxo-17-(2-furyl)-18,19,20-trinor-prostadien-16-inic acid
(5Z,13E)-(8R,11R, 12R,15R)-11,15-dihydroxy-15-methyl-9-oxo-17-(2-furyl)-18,19,20-trinor-prostadien-16-inic acid
(5Z,13E)-(8R,11R,12R,15S)-11,15-dihydroxy-15-methyl-9-oxo-17-(2-pyridyl)-18,19,20-trinor-prostadien-16-inic acid
(5Z,13E)-(8R,11R,12R,15R)-11,15-dihydroxy-15-methyl-9-oxo-17-(2-pyridyl)-18,19,20-trinor-prostadien-16-inic acid
(5Z,13E)-(8R,11R,12R,15S)-11,15-dihydroxy-15-methyl-9-oxo-17-ethoxy-18,19,20-trinor-prostadien-16-inic acid
(5Z,13E)-(8R,11R,12R,15R)-11,15-dihydroxy-15-methyl-9-oxo-17-ethoxy-18,19,20-trinor-prostadien-16-inic acid
(5Z,13E)-(8R,11R,12R,15S)-11,15-dihydroxy-15-methyl-9-oxo-17-phenoxy-18,19,20-trinor-prostadien-16-inic acid
(5Z,13E)-(8R,11R,12R,15R)-11,15-dihydroxy-15-methyl-9-oxo-17-phenoxy-18,19,20-trinor-prostadien-16-inic acid
(5Z,13E)-(8R,11R,12R,15S)-11,15-dihydroxy-18,18-dimethyl-15-methyl-9-oxo-20-nor-prostadien-16-inic acid
(5Z,13E)-(8R,11R,12R,15R)-11,15-dihydroxy-18,18-dimethyl-15-methyl-9-oxo-20-nor-prostadien-16-inic acid
(5Z,13E)-(8R,11R,12R15S)-11,15-dihydroxy-15-methyl-17-cyclohexyl-9-oxo-18,19,20-trinor-prostadien-16-inic acid
(5Z,13E)-(8R,11R12R,15R)-11,15-dihydroxy-15-methyl-17-cyclohexyl-9-oxo-18,19,20-trinor-prostadien-16-inic acid
(5Z)-(8R,11R,12R,15S)-11,15-dihydroxy-15-methyl-9-oxoprosten-16-inic acid
(5Z)-(8R,11R,12R,15R)-11,15-dihydroxy-15-methyl-9-oxoprosten-16-inic acid
(13E)-(8R, 11R,12R15S)-11,15-dihydroxy-15-methyl-9-oxoprosten-16-inic acid
(13E)-)8R,11R,12R,15R)-11,15-dihydroxy-15-methyl-9-oxoprosten-16-inic acid
(8R,11R,12R,15S)-11,15-dihydroxy-15-methyl-9-oxo-prostan-16-inic acid
(8R,11R,12R,15R)-11,15-dihydroxy-15-methyl-9-oxo-prostan-16-inic acid.

EXAMPLE 24

(5Z,13E)-(8R,11R,12R,15S)-11,15-Dihydroxy-9-oxoprostadien-16-inic Acid 1.5 ml. of N-trimethylsilyldiethylamine was added dropwise to a solution, cooled to -40°, of 220 mg. of (5Z,13E)-(8R,11R,12R,15S)-9,11,15-trihydroxy-prostadien-16-inic acid (prepared according to Example 20, page 72, line 9) in 15 ml. of absolute acetone.

The mixture was agitated for 6 hours at −35° and then evaporated to dryness under vacuum. The 11,15-bis(trimethylsilyl ether) obtained in this way was oxidized in the 9-position without further purification. 1.20 g. of Collins reagent (Tetrahedron Letters 1968, 3363) was dissolved in 12 ml. of absolute methylene chloride and, under agitation at +10°, a solution of the 11,15-bis(dimethylsilyl ether) in 20 ml. of methylene chloride was added thereto. After 10 minutes, the mixture was diluted with 100 ml. of ether, filtered, and evaporated under vacuum. The residue was agitated for 16 hours with 30 ml. of 70% ethanol at room temperature under argon, concentrated under vacuum, and 50 ml. of saturated ammonium chloride solution was added thereto. The mixture was extracted three times with respectively 50 ml. of ether. The organic extract was shaken twice with respectively 20 ml. of saturated NaCl solution, dried over magnesium sulfate, and evaporated under vacuum. After chromatography on silica gel (deactivated wth 3% water) with methylene chloride/ethyl acetate (9+1), 92 mg. of the title compound was obtained as a colorless oil.

TLC (chloroform/isopropanol 85+15): Rf value 0.45
IR: 3600-3300, 3000, 2960, 2940, 2240, 1740, 1710, 975 cm$^{-1}$.

EXAMPLE 25

(5Z,13E)-(8R,11R,12R,15R)-11,15-Dihydroxy-9-oxo-prostadien-16-inic Acid.

In accordance with the process described in Example 24, 79 mg. of the title compound was obtained as a colorless oil from 164 mg. of (5Z,13E)-(8R,9S11R,12R,15R)-9,11,15-trihydroxy-prostadien-16-inic acid (prepared according to Example 20).

TLC (chloroform/isopropanol 85+15): Rf value 0.43
IR: 3600-3300, 3000, 2960, 2940, 2240, 1740, 1710, 975 cm$^{-1}$.

EXAMPLE 26

Analogously to the method described in Example 24, the following 9-oxo-compounds were produced from the 11-hydroxy-compounds mentioned in Example 20:
(5Z,13E)-(8R,11R,12R,15S)-11,15-dihydroxy-20-ethyl-9-oxoprostadien-16-inic acid
(5Z,13E)-(8R,11R,12R,15R)-11,15-dihydroxy-20-ethyl-9-oxoprostadien-16-inic acid
(5Z,13E)-(8R,11R,12R,15S)-11,15-dihydroxy-20-methyl-9-oxoprostadien-16-inic acid
(5Z,13E)-(8R,11R,12R,15R)-11,15-dihydroxy-20-methyl-9-oxoprostadien-16-inic acid
(5Z,13E)-(8R,11R,12R,15S)-11,15-dihydroxy-9-oxo-17-(2-furyl)-18,19,20-trinor-prostadien-16-inic acid
(5Z,13E)-(8R,11R,12R15R)-11,15-dihydroxy-9-oxo-17-(2-furyl)-18,19,20-trinor-prostadien-16-inic acid
(5Z,13E)-(8R,11R,12R,15S)-11,15-dihydroxy-9-oxo-17-(2-thienyl)-18,19,20,trinor-prostadien-16-inic acid
(5Z,13E)-(8R,11R,12R,15R)-11,15-dihydroxy-9-oxo-17-(2-thienyl)-18,19,20-trinor-prostadien-16-inic acid
(5Z,13E)-(8R,11R,12R,15S)-11,15-dihydroxy-9-oxo-17-(2-pyridyl)-18,19,20-trinor-prostadien-16-inic acid
(5Z,13E)-(8R,11r,12R,15R)-11,15-dihydroxy-9-oxo-17-(2-pyridyl)-18,19,20-trinor-prostadien-16-inic acid
(5Z,13E)-(8R,11R,12R,15S)-11,15-dihydroxy-17-ethoxy-9-oxo-18,19,20-trinor-prostadien-16-inic acid
(5Z,13E)-(8R,11R,12R,15R)-11,15-dihydroxy-17-ethoxy-9-oxo-18,19,20-trinor-prostadien-16-inic acid
(5Z,13E)-(8R,11R,12R,15S)-11,15-dihydroxy-9-oxo-17-phenoxy-18,19,20-trinor-prostadien-16-inic acid
(5Z,13E)-(8R,11R,12R,15R)-11,15-dihydroxy-9-oxo-17-phenoxy-18,19,20-trinor-prostadien-16-inic acid
(5Z,13E)-(8R,11R,12R,15S)-11,15-dihydroxy-9-oxo-17-cyclohexyl- 18,19,20-trinor-prostadien-16-inic acid
(5Z,13E)-(8R,11R,12R,15R)-11,15-dihydroxy-9-oxo-17-cyclohexyl-18,19,20-trinor-prostadien-16-inic acid
(5Z,13E)-(8R,11R12R,15S)-11,15-dihydroxy-18,18-dimethyl-9-oxo-20-nor-prostadien-16-inic acid
(5Z,13R)-(8R,11R,12R,15R)-11,15-dihydroxy-18,18-dimethyl-9-oxo-20-nor-prostadien-16-inic acid
(5Z)-(8R,11R,12R,15S)-11,15-dihydroxy-9-oxo-prosten-16-inic acid
(5Z)-(8R,11R,12R,15R)-11,15-dihydroxy-9-oxo-prosten-16-inic acid
(13E)-(8R,11R,12R,15S)-11,15-dihydroxy-9-oxo-prosten-16-inic acid
(13E)-(8R,11R,12R,15R)-11,15-dihydroxy-9-oxo-prosten-16-inic acid
(8R,11R,12R,15S)-11,15-dihydroxy-9-oxo-prostan-16-inic acid
(8R, 11R,12R,15R)-11,15-dihydroxy-9-oxo-prostan-16-inic acid.

EXAMPLE 27

Methyl Ester of (5Z,13E)-(8R,9S,12R,15S)-9,15-Dihydroxy-15-methyl-11-oxo-17-phenyl-18,19,20-trinor-prostadien-16-inic Acid At 0°, a solution of 400 mg. of the methyl ester of (5Z,13E)-(8R,9S,11R,12R,15S)-9,11,15-trihydroxy-15-methyl-17-phenyl-18,19,20-trinor-prostadien-16-inic acid (prepared analogously to Example 1) in 5ml. of dry methylene chloride was added under agitation to a solution of 2 g. of freshly prepared Collins reagent (Tetrahedron Letters 1968, 3363) in 25 ml. of dry methylene chloride. The mixture was stirred for 15 minutes at 0°, diluted with 200 ml. of ether, filtered, and the filtrate shaken twice with respectively 30 ml. of 5% sodium bicarbonate solution and 3x with respectively 40 ml. of saturated NaCl solution, dried over sodium sulfate, and evaporated under vacuum. Chromatography of the residue on silica gel (deactivated with 3% water) yielded, with ether, 197 mg. of the title compound as a colorless oil.

TLC (ether): Rf value 0.65
IR: 3600, 3030, 2950, 2238, 1735, 1598, 978 cm$^{-1}$.

EXAMPLE 28

Methyl Ester of (5Z,13E)-(8R,9S, 12R,15R)-9,15-Dihydroxy-15-methyl-11-oxo-17-phenyl-18,19,20-trinor-prostadien-16-inic Acid According to the process described in Example 27, 178 mg. of the title compound was obtained as a colorless oil from 390 mg. of the 15R-configured compound described in Example 27.

TLC (ether): Rf value 0.60
IR: 3600, 3030, 2950, 2238, 1735, 1598, 978 cm$^{-1}$.

EXAMPLE 29

Methyl Ester of (5Z,13E)-(8R,9S,12R,15S)-9,15-Dihydroxy-15-methyl-11-oxo-prostadien-16-inic Acid In accordance with the method set forth in Example 27, 95 mg. of the title compound was produced as a colorless oil from 220 mg. of the 15S-configured compound prepared according to Example 1.

TLC (ether): Rf value 0.66
IR: 3600, 2998, 2950, 2240, 1735, 978 cm$^{-1}$.

EXAMPLE 30

Methyl Ester of (5Z,13E)-(8R,9S,12R,15R)-9,15-Dihydroxy-15-methyl-11-oxo-prostadien-16-inic Acid According to the process set forth in Example 27, 81 mg. of the title compound was obtained as a colorless oil from 180 mg. of the 15R-configured compound prepared in accordance with Example 1.

TLC (ether): Rf value 0.64
IR: 3600, 2998, 2240, 1735, 978 cm$^{-1}$.

EXAMPLE 31

Methyl Ester of (5Z,13E)-(8R,11R,12R,15S)-11,15-Dihydroxy-15-methyl-9-oxo-prostadien-16-inic Acid At 0°, 5 ml. of an ethereal diazomethane solution ("Organikum" p. 528, publishers: Deutscher Verlag der Wissenschaften) was added dropwise to a solution of 180 mg. of the 15S-configured compound obtained as described in Example 21 in 10 ml. of methylene chloride. After 5 minutes, the reaction mixture was evaporated to dryness under vacuum. After filtration over silica gel (deactivated with 3% water), 165 mg. of the title compound was obtained with ether as a colorless oil.

TLC (ether): Rf value 0.53
IR: 3600, 3000, 2960, 2940, 2240, 1735, 975 cm$^{-1}$.

EXAMPLE 32

Methyl Ester of (5Z,13E)-(8R,11R,12R,15R)-11,15-Dihydroxy-15-methyl-9-oxo-prostadien-16-inic Acid With diazomethane, 85 mg. of the title compound was obtained as a colorless oil from 92 mg. of the 15R-configured compound obtained according to Example 31.

TLC (ether): Rf value 0.50
IR: 3600, 3000, 2960, 2940, 2240, 1735, 975 cm$^{-1}$.

EXAMPLE 33

Analogously to Example 31, the following compounds are obtained from the aforementioned prostaglandin E acids:

the methyl ester of each of the following:

(5Z,13E)-(8R,11R,12R,15S)-11,15-dihydroxy-15-methyl-20-ethyl-9-oxo-prostadien-16-inic acid
(5Z,13E)-(8R,11R,12R,15R)-11,15-dihydroxy-15-methyl-20-ethyl-9-oxo-prostadien-16-inic acid
(5Z,13E)-(8R,11R,12R,15S)-11,15-dihydroxy-15,20-dimethyl-9-oxoprostadien-16-inic acid
(5Z,13E)-(8R,11R,12R,15R)-11,15-dihydroxy-15,20-dimethyl-9-oxo-prostadien-16-inic acid
(5Z,13E)-(8R,11R,12R,15S)-11,15-dihydroxy-15-methyl-9-oxo-17-(2-thienyl)-18,19,20-trinor-prostadien-16-inic acid
(5Z,13E)-(8R,11R,12R,15R)-11,15-dihydroxy-15-methyl-9-oxo-17-(2-thienyl)-18,19,29-trinor-prostadien-16-inic acid
(5Z,13E)-(8R,11R,12R,15S)-11,15-dihydroxy-15-methyl-9-oxo-17-(2-furyl)-18,19,20-trinor-prostadien-16-inic acid
(5Z,13E)-(8R,11R,12R,15R)-11,15-dihydroxy-15-methyl-9-oxo-17-(2-furyl)-18,19,20-trinor-prostadien-16-inic acid
(5Z,13E)-(8R,11R,12R,15S)-11,15-dihydroxy-15-methyl-9-oxo-17-(2-pyridyl)-18,19,20-trinor-prostadien-16-inic acid
(5Z,13E)-(8R,11R,12R,15R)-11,15-dihydroxy-15-methyl-9-oxo-17-(2-pyridyl)-18,19,20-trinor-prostadien-16-inic acid
(5Z,13E)-(8R,11R,12R,15S)-11,15-dihydroxy-15-methyl-9-oxo-17-ethoxy-18,19,20-trinor-prostadien-16-inic acid
(5Z,13E)-(8R,11R,12R,15R)-11,15-dihydroxy-15-methyl-9-oxo-17-ethoxy-18,19,20-trinor-prostadien-16-inic acid
(5Z,13E)-(8R,11R,12R,15S)-11,15-dihydroxy-15-methyl-9-oxo-17-phenoxy-18,19,20-trinor-prostadien-16-inic acid
(5Z,13E)-(8R,11R,12R,15R)-11,15-dihydroxy-15-methyl-9-oxo-17-phenoxy-18,19,20-trinor-prostadien-16-inic acid
(5Z,13E)-(8R,11R,12R,15S)-11,15-dihydroxy-18,18-dimethyl-15-methyl-9-oxo-20-nor-prostadien-16-inic acid
(5Z,13E)-(8R,11R,12R,15R)-11,15-dihydroxy-18,18-dimethyl-15-methyl-9-oxo-20-nor-prostadien-16-inic acid
(5Z,13E)-(8R,11R,12R,15S)-11,15-dihydroxy-15-methyl-17-cyclohexyl-9-oxo-18,19,20-trinor-prostadien-16-inic acid
(5Z,13E)-(8R, 11R,12R,15R)-11,15-dihydroxy-15-methyl-17-cyclohexyl-9-oxo-18,19,20-trinor-prostadien-16-inic acid
(5Z)-(8R,11R,12R,15S)-11,15-dihydroxy-15-methyl-9-oxo-prosten-16--inic acid
(5Z)-(8R,11R,12R,15R)-11,15-dihydroxy-15-methyl-9-oxo-prosten-16-inic acid
(13E)-(8R,11R,12R,15S)-11,15-dihydroxy-15-methyl-9-oxo-prosten-16-inic acid
(13E)-(8R,11R,12R,15R)-11,15-dihydroxy-15-methyl-9-oxo-prosten-16-inic acid
(8R,11R,12R,15S)-11,15-dihydroxy-15-methyl-9-oxo-prostan-16-inic acid
(8R,11R,12R,15R)-11,15-dihydroxy-15-methyl-9-oxo-prostan-16-inic acid
(5Z,13E)-(8R,11R,12R,15S)-11,15-dihydroxy-9-oxo-prostadien-16-inic acid
(5Z,13E)-(8R,11R,12R,15R)-b 11,15-dihydroxy-9-oxo-prostadien-16-inic acid
(5Z,13E)-(8R,11R,12R,15R)-11,15-dihydroxy-20-methyl-9-oxo-prostadien-16-inic acid
(5Z,13E)-(8R,11R,12R,15S)-11,15-dihydroxy-20-ethyl-9-oxoprostadien-16-inic acid
(5Z,13E)-(8R,11R,12R,15S)-11,15-dihydroxy-20-methyl-9-oxo-prostadien-16-inic acid
(5Z,13E)-(8R,11R,12R,15R)-11,15-dihydroxy-20-methyl-9-oxoprostadien-16-inic acid
(5Z,13E)-(8R,11R,12R,15S)-11,15-dihydroxy-9-oxo-17-(2-furyl)-18,19,20-trinor-prostadien-16-inic acid
(5Z,13E)-(8R,11R,12R,15R)-11,15-dihydroxy-9-oxo-17-(2-furyl)-18,19,20-trinor-prostadien-16-inic acid
(5Z,13E)-(8R,11R,12R,15S)-11,15-dihydroxy-9-oxo-17-(2-thienyl)-18,19,20-trinor-prostadien-16-inic acid
(5Z,13E)-(8R,11R,12R,15R)-11,15-dihydroxy-9-oxo-17-(2-thienyl)-18,19,20-trinor-prostadien-16-inic acid
(5Z,13E)-(8R,11R,12R,15S)-11,15-dihydroxy-9-oxo-17-(2-pyridyl)-18,19,20-trinor-prostadien-16-inic acid
(5Z,13E)-(8R,11R,12R,15R)-11,15-dihydroxy-9-oxo-17-(2-pyridyl)-18,19,20-trinor-prostadien-16-inic acid
(5Z,13E)-(8R,11R,12R,15S)-11,15-dihydroxy-17-ethoxy-9-oxo-18,19,20-trinor-prostadien-16-inic acid (5Z,13E)-(8R,11R,12R,15R)-11,15-dihydroxy-17-ethoxy-9-oxo-18,19,20-trinor-prostadien-16-inic acid
(5Z,13E)-(8R,11R,12R,15S)-11,15-dihydroxy-9-oxo-17-phenoxy-18,19,20-trinor-prostadien-16-inic acid
(5Z,13E)-(8R,11R,12R,15R)-11,15-dihydroxy-9-oxo-17-phenoxy-18,19,20-trinor-prostadien-16-inic acid
(5Z,13E)-(8R,11R,12R,15S)-11,15-dihydroxy-9-oxo-17-cyclohexyl-18,19,20-trinor-prostadien-16-inic acid
(5Z,13E)-(8R,11R,12R,15R)-11,15-dihydroxy-9-oxo-17-cyclohexyl-18,19,20-trinor-prostadien-16-inic acid
(5Z,13E)-(8R,11R,12R,15S)-11,15-dihydroxy-18,18-dimethyl-9-oxo-20-nor-prostadien-16-inic acid
(5Z,13E)-(8R,11R,12R15R)-11,15-dihydroxy-18,18-dimethyl-9-oxo-20-nor-prostadien-16-inic acid
(5Z)-(8R,11R,12R,15S)-11,15-dihydroxy-9-oxo-prosten-16-inic acid
(5Z)-(8R,11R,12R,15R)-11,15-dihydroxy-9-oxo-prosten-16-inic acid
(13E-(8R,11R,12R,15S)-11,15-dihydroxy-9-oxo-prosten-16-inic acid
(13E)-(8R,11R,12R,15R)-11,15-dihydroxy-9-oxo-prosten-16-inic acid
(8R,11R,12R,15S)-11,15-dihydroxy-9-oxo-prostan-16-inic acid
(8R,11R,12R,15R)-11,15dihydroxy-9-oxo-prostan-16-inic acid.

EXAMPLE 34

Methyl Ester of (5Z,10Z,13E)-(8R,12R,15S)-15-Hydroxy-9-oxo-15-methyl-prostatrien-16-inic Acid A solution of 110 mg. of the compound prepared according to Example 31 in 3 ml. of pyridine was combined with 1 ml. of acetic anhydride, and the reaction mixture was allowed to stand for 6 hours at room temperature and then evaporated to dryness under vacuum. After purification of the residue by layer chromatography (ether/hexane 7+3), 72 mg. of the title compound was obtained as a colorless oil.

TLC (ether: Rf value 0.66
IR: 3600, 2998, 2955, 2935, 2240, 1730, 1700, 1585, 975 cm$^{-1}$.

EXAMPLE 35

Methyl Ester of (5Z,10Z,13E)-(8R,12R,15R)-15-Hydroxy-9-oxo-15-methyl-prostatrien-16-inic Acid In analogy to Example 34, 75 mg. of the title compound was obtained as a colorless oil from 100 mg. of the compound prepared according to Example 33.

TLC (ether): Rf value 0.63
IR: 3600, 2998, 2955, 2935, 2240, 1730, 1700, 1585, 975 cm$^{-1}$.

EXAMPLE 36 p-Phenylphenacyl Ester of (5Z,13E)-(8R,9S,11R,12R,15S)-9,11,15-Trihydroxy-15-methyl-17-phenyl-18,19,20-trinor-prostadien-16-inic Acid At 20° under argon, 100 mg. of (5Z,13E)-(8R,9S,11R,12R,15S)-9,11,15-trihydroxy-15-methyl-17-phenyl-18,19,20-trinor-prostadien-16-inic acid was agitated with 28 mg. of triethylamine and 80 mg. of p-phenylphenacyl bromide in 6 ml. of acetone for 14 hours. After dilution with water, the mixture was extracted with ether, and the ether extract was shaken twice with water, dried over magnesium sulfate, and evaporated under vacuum. After chromatography on silica gel (deactivated with 3% water), 82 mg. of the title compound was obtained with ether/ethyl acetate (8+2) as a waxy mass.

TLC (ether/dioxane 8+2): Rf value 0.41
IR: 3600, 3450 (wide), 3030, 2935, 2240, 1740, 1695, 1600, 978 cm$^{-1}$.

Analogously the p-phenylphenacyl esters of the prostaglandin acids prepared according to Examples 3, 16 – 26 are obtained.

EXAMPLE 37

(4-Biphenylyl) Ester of (5Z,13E)-(8R,9S,11R,12R,15S)-9,11,15-Trihydroxy-15-methyl-17-phenyl-18,19,20-trinor-prostadien-16-inic acid At 0°, 150 mg. of (5Z,13E)-(8R,9S,11R,12R,15S)-9,11,15-trihydroxy-15-methyl-17-phenyl-18,19,20-trinor-prostadien-16-inic acid dissolved in 20 ml. of chloroform, was combined with 150 mg. of dicyclohexylcarbodiimide. After one hour, 1.5 g. of p-phenylphenol and 0.75 ml. of pyridine were added thereto, and the mixture was stirred fpr 6 hours at room temperature. After filtering the reaction mixture over silica gel (deactivated with 3% water) with chloroform/isopropanol (9+1), the thus preliminarily purified reaction product was chromatographed on silica gel (deactived with 3% water). With ether/ethyl acetate (8+2), 95 mg. of the title compound was obtained as a colorless, viscous oil.

TLC (ether/dioxane 8+2): Rf value 0.44.
IR: 3600, 3450 (wide), 3030, 2998, 2940, 2240, 1750, 1600, 1485, 978 cm$^{-1}$.

Analogously the (4-biphenylyl) esters of the prostaglandin acids prepared according to Examples 3, 16 – 26 are obtained.

EXAMPLE 38

Tris(hydroxymethyl)aminomethane Salt of (5Z,13E)-(8R,9S,11R,12R,15S)-9,11,15-Trihydroxy-15-methyl-prostadien-16-inic Acid At 60°, a solution of 62 mg. of tris(hydroxymethyl)aminomethane in 0.2 ml. of water was added to a solution of 200 mg. of the prostaglandin acid prepared according to Example 16 in 28 ml. of acetonitrile. The reaction mixture was then allowed to stand for 14 hours at room temperature and thereafter was filtered, the residue was treated with acetonitrile, and dried under vacuum, thus obtaining 148 mg. of the title compound as a white powder.

EXAMPLE 39

Analogously to Example 38, the tris(hydroxymethyl)aminomethane salts of the following prostaglandin acids disclosed in the preceding examples were obtained:
(5Z,13E)-(8R,9S,11R,12R,15S)-9,11,15-trihydroxy-15-methyl-prostadien-16-inic acid
(5Z,13E)-(8R,9S,11R,12R,15R)-9,11,15-trihydroxy-15-methyl-prostadien-16-inic acid.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A (5Z, 13E) prostaglandin compound of the formula

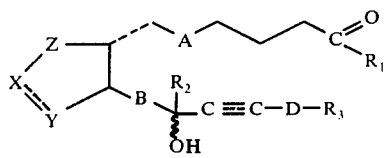

wherein R₁ is —OR₅ or —O—CH₂—U—V, R₅ being a hydrogen atom, alkyl of 1-10 carbon atoms, phenyl, 1-naphthyl or 2-naphthyl, each of which can be substituted by up to 3 of halogen, phenyl, alkyl of 1-4 carbon atoms, chloromethyl, fluoromethyl, trifluoromethyl, carboxy, alkoxy and hydroxy or a heterocyclic ring of 5 or 6 ring members whose heteroatom is N, O or S, U being a direct bond, carbonyl or carbonyloxy, and V being phenyl substituted by one or more of phenyl, alkoxy of 1-2 carbon atoms, and halogen;

R₂ is hydrogen or alkyl of 1-5 carbon atoms;
R₃ is alkyl or cycloalkyl of up to 10 carbon atoms;
A is cis-CH=CH—; B is trans-CH=CH;
D is a direct bond, oxygen, or sulfur;
Z is carbonyl or >CH〜OR₄ wherein OR₄ is in the α- or β-position and R₄ is H, tetrahydropyranyl, tetrahydrofuranyl, α-ethoxyethyl, trimethylsilyl, and tri-p-xylysilyl, alkanoyl of up to 7 carbon atoms or benzoyl; and
X====Y is

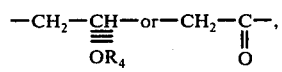

when Z is >CH〜OR₄—, or

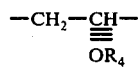

or —CH=CH—, when Z is carbonyl;
and, when R₁ is hydroxy, physiologically acceptable salts thereof with bases.

2. (5Z,13E)-(8R,9S,11R,12R,15R)-9,11,15-Trihydroxy-18,18-dimethyl-20-nor-prostadien-16-inic acid, a compound of claim 1.

3. Methyl ester of (5Z,13E)-(8R,9S,11R,12R,15S)-9,11,15-trihydroxy-15-methyl-prostadien-16-inic acid, a compound of claim 1.

4. Methyl ester of (5Z,13E)-(8R,9S,11R,12R,15R)-9,11,15-trihydroxy-15-methyl-prostadien-16-inic acid, a compound of claim 1.

5. Methyl ester of (5Z,13E)-(8R,9S,11R,12R,15S)-9,11,15-trihydroxy-15,20-dimethyl-prostadien-16-inic acid, a compound of claim 1.

6. Methyl ester of (5Z,13E)-(8R,9S,11R,12R,15R)-9,11,15-trihydroxy-15,20-dimethyl-prostadien-16-inic acid, a compound of claim 1.

7. Methyl ester of (5Z,13E)-(8R,9S,11R,12R,15S)-9,11,15-trihydroxy-20-ethyl-15-methyl-prostadien-16-inic acid, a compound of claim 1.

8. Methyl ester of (5Z,13E)-(8R,9S,11R,12R,15R)-9,11,15-trihydroxy-20-ethyl-15-methyl-prostadien-16-inic acid, a compound of claim 1.

9. Methyl ester of (5Z,13E)-(8R,9S,11R,12R,15S)-9,11,15-trihydroxy-15-methyl-17-ethoxy-18,19,20-trinorprostadienl-16-inic acid, a compound of claim 1.

10. Methyl ester of (5Z,13E)-(8R,9S,11R,12R,15R)-9,11,15-Trihydroxy-15-methyl-17-ethoxy-18,19,20-trinorprostadien-16-inic acid, a compound of claim 1.

11. Methyl ester of (5Z,13E)-(8R,9S,11R,12R,15S)-9,11,15-trihydroxy-15-methyl-17-cyclohexyl-18,19,20-trinorprostadien-16-inic acid, a compound of claim 1.

12. Methyl ester of (5Z,13E)-(8R,9S,11R,12R,15R)-9,11,15-trihydroxy-15-methyl-17-cyclohexyl-18,19,20-trinorprostadien-16-inic acid, a compound of claim 1.

13. Methyl ester of (5Z,13E)-(8R,9S,11R,12R,15S)-9,11,15-trihydroxy-18,18-dimethyl-15-methyl-20-nor-prostadien-16-inic acid, a compound of claim 1.

14. Methyl ester of (5Z,13E)-(8R,9S,11R,12R,15R)-9,11,15-trihydroxy-18,18-dimethyl-15-methyl-20-nor-prostadien-16-inic acid, a compound of claim 1.

15. Methyl ester of (5Z,13E)-(8R,9S,11R,12R,15S)-9,11,15-trihydroxy-prostadien-16-inic acid, a compound of claim 1.

16. Methyl ester of (5Z,13E)-(8R,9S,11R,12R,15R)-9,11,15-trihydroxy-prostadien-16-inic acid, a compound of claim 1.

17. Methyl ester of (5Z,13E)-(8R,9S,11R,12R,15S)-9,11,15-trihydroxy-20-ethyl-prostadien-16-inic acid, a compound of claim 1.

18. Methyl ester of (5Z,13E)-(8R,9S,11R,12R,15R)-9,11,15-trihydroxy-20-ethyl-prostadien-16-inic acid, a compound of claim 1.

19. Methyl ester of (5Z,13E)-(8R,9S,11R,12R,15S)-9,11,15-trihydroxy-20-methyl-prostadien-16-inic acid, a compound of claim 1.

20. Methyl ester of (5Z,13E)-(8R,9S,11R,12R,15R)-9,11,15-trihydroxy-20-methyl-prostadien-16-inic acid, a compound of claim 1.

21. Methyl ester of (5Z,13E)-(8R,9S,11R,12R,15S)-9,11,15-trihydroxy-17-ethoxy-18,19,20-trinor-prostadien-16-inic acid, a compound of claim 1.

22. Methyl ester of (5Z,13E)-(8R,9S,11R,12R,15R)-9,11,15-trihydroxy-17-ethoxy-18,19,20-trinor-prostadien-16-inic acid, a compound of claim 1.

23. Methyl ester of (5Z,13E)-(8R,9S,11R,12R,15S)-9,11,15-trihydroxy-17-cyclohexyl-18,19,20-trinor-prostadien-16inic acid, a compound of claim 1.

24. Methyl ester of (5Z,13E)-(8R,9S,11R,12R,15R)-9,11,15-trihydroxy-17-cyclohexyl-18,19,20-trinor-prostadien-16-inic acid, a compound of claim 1.

25. Methyl ester of (5Z,13E)-(8R,9S,11R,12R,15S)-9,11,15-trihydroxy-18,18-dimethyl-20-nor-prostadien-16-inic acid, a compound of claim 1.

26. Methyl ester of (5Z,13E)-(8R,9S,11R,12R,15R)-9,11,15-trihydroxy-18,18-dimethyl-20-nor-prostadien-16-inic acid, a compound of claim 1.

27. (5Z,13E)-(8R,9S,11R,12R,15S)-9,11,15-Trihydroxy-15-methyl-prostadien-16-inic acid, a compound of claim 1.

28. (5Z,13E)-(8R,9S,11R,12R,15R)-9,11,15-Trihydroxy-15-methyl-prostadien-16-inic acid, a compound of claim 1.

29. (5Z,13E)-(8R,9S,11R,12R,15S)-9,11,15-Trihydroxy-20-ethyl-15-methyl-prostadien-16-inic acid, a compound of claim 1.

30. (5Z,13E)-(8R,9S,11R,12R,15R)-9,11,15-Trihydroxy-20-ethyl-15-methyl-prostadien-16-inic acid, a compound of claim 1.

UNITED STATES PATENT AND TRADEMARK OFFICE
CERTIFICATE OF CORRECTION

PATENT NO. : 4,073,934
DATED : February 14, 1978
INVENTOR(S) : WERNER SKUBALLA ET AL.

It is certified that error appears in the above-identified patent and that said Letters Patent are hereby corrected as shown below:

Claim 35, column 45, line 13: "(8R, 9S, 11R, 15S)"
        should read: -- (8R, 9S, 11R, 12R, 15S) --.

Claim 37, column 45, line 19: "(8R, 9S, 11R, 15S)"
        should read: -- (8R, 9S, 11R, 12R, 15S) --.

Signed and Sealed this

Sixth Day of June 1978

[SEAL]

Attest:

RUTH C. MASON
*Attesting Officer*

DONALD W. BANNER
*Commissioner of Patents and Trademarks*

UNITED STATES PATENT AND TRADEMARK OFFICE
CERTIFICATE OF CORRECTION

PATENT NO. : 4,073,934

DATED : February 14, 1978

INVENTOR(S) : WERNER SKUBALLA ET AL.

It is certified that error appears in the above—identified patent and that said Letters Patent are hereby corrected as shown below:

Claim 35, column 45, line 13: "(8R, 9S, 11R, 15S)"
should read: -- (8R, 9S, 11R, 12R, 15S) --.

Claim 37, column 45, line 19: "(8R, 9S, 11R, 15S)"
should read: -- (8R, 9S, 11R, 12R, 15S) --.

Signed and Sealed this

Sixth Day of June 1978

[SEAL]

Attest:

RUTH C. MASON
*Attesting Officer*

DONALD W. BANNER
*Commissioner of Patents and Trademarks*